US006645745B1

(12) United States Patent
Wojnowski et al.

(10) Patent No.: US 6,645,745 B1
(45) Date of Patent: Nov. 11, 2003

(54) IDENTIFICATION OF A NEW MEMBER OF THE CYTOCHROME P450 3A (CYP3A) GENE FAMILY: CYP3AX

(75) Inventors: Leszek Wojnowski, Munich (DE); Klaus Gellner, Peissenberg (DE); Regina Eiselt, Eurasburg (DE)

(73) Assignee: Epidauros Biotechnologie AG, Bernried (DE)

( * ) Notice: Subject to any disclaimer, the term of this patent is extended or adjusted under 35 U.S.C. 154(b) by 0 days.

(21) Appl. No.: 09/583,447

(22) Filed: May 30, 2000

(51) Int. Cl.[7] .............................. C12N 9/00; C12N 1/20; C12N 15/00; C12P 21/04; C07H 21/04

(52) U.S. Cl. ................. 435/183; 435/252.3; 435/320.1; 435/6; 435/71.1; 536/23.2; 536/23.1

(58) Field of Search .............................. 435/183, 252.3, 435/320.1, 6; 536/23.2; 424/94.6

(56) References Cited

U.S. PATENT DOCUMENTS 5,538,885 A * 7/1996 Hollis et al. .............. 435/240.2

FOREIGN PATENT DOCUMENTS

| WO | WO 94/29469 | 12/1994 |
| WO | WO 97/00957 | 1/1997 |

OTHER PUBLICATIONS

Washington University Genome Sequencing Ceter. Est database—Accession #A1I861809 (1999).*
Igarashi et al. Marmoset liver cytochrome P450s: study for expression and molecular cloning of their cDNAs. Archives of biochemistry and biophysics, vol. 339, No. 1, Mar. 1, pp. 85–91 (1997).*
Anderson, "Human Gene Therapy," *Science* 256(5058):808–813, May 8, 1992.
Berks, "Patent Information in Biotechnology," *TIBTECH* 12(9):352–364, Sep. 1994.
Berry et al., "A Prototype Computer System for de novo Protein Design," *Biolchem Soc Trans.* 22(4):1033–1036, Nov. 1994.
Bertilsson et al., "Identification of a Human Nuclear Receptor Defines a New Signaling Pathway for CYP3A Induction," *Proc. Natl. Acad. Sci. USA* 95(21):12208–12213, Oct. 13, 1998.

(List continued on next page.)

Primary Examiner—Ponnathapu Achutamurthy
Assistant Examiner—Yong D Pak
(74) Attorney, Agent, or Firm—Fish & Neave; James F. Haley, Jr.; Jane T. Gunnison

(57) ABSTRACT

The present invention relates to polynucleotides encoding the CYP3AX protein and variants thereof. Further, the present invention also provides vectors comprising said polynucleotides, in particular vectors, wherein polynucleotides of the present invention are operatively linked to regulatory elements allowing expression in prokaryotic and/or eukaryotic host cells. In addition, the present invention relates to proteins encoded by said polynucleotides and antibodies specifically recognizing such proteins. The present invention also concerns transgenic non-human animals comprising the above-described polynucleotide or vectors. Moreover, the present invention relates to methods for identifying and obtaining drug candidates and inhibitors for therapy of disorders related to the malfunction of the CYP3AX genes as well as to methods of diagnosing the status of such disorders. The present invention also relates to methods for the identification of molecular variants of the CYP3AX polynucleotide or protein. The present invention furthermore provides pharmaceutical and diagnostic compositions comprising the above-described polynucleotides, vectors, proteins, antibodies, drugs and inhibitors obtainable by the above-described method. Said compositions are particularly useful for diagnosing and treating various diseases with drugs that are substrates, inhibitors or modulators of CYP3AX genes or their product.

22 Claims, 8 Drawing Sheets

OTHER PUBLICATIONS

Bertz et al., "Use of in vitro and in vivo Data to Estimate the Likelihood of Metabolic Pharmacokinetic Interactions," *Clin Pharmacokinet.* 32(3):210–258, Mar. 1997.

Brutlag et al. "Improved Sensitivity of Biological Sequence Database Searches," *CABIOS* 6(3):237–245, Jul. 1990.

Crespi et al., "Development of Caco–2 Cells Expressing High Levels of cDNA–Derived Cytochrome P4503A4," *Pharm Res.* 13(11):1635–1641, Nov. 1996.

Crooke et al., "Pharmacokinetic Properties of Several Novel Oligonucleotide Analogs in Mice," *J Pharmacol Exp Ther.* 277(2):923–937, May 1996.

Cunningham et al., "High–Resolution Epitope Mapping of hGH–Receptor Interactions by Alanine–Scanning Mutagenesis," *Science* 244(4908):1081–1085, Jun. 2, 1989.

Daly et al., "Recent Advances in Understanding the Molecular Basis of Polymorphisms in Genes Encoding Cytochrome P450 Enzymes," *Toxicology Letters* 102–103:143–147, Dec. 28, 1998.

Dörner et al., "The Synthesis of Peptidomimetic Combinatorial Libraries Through Successive Amide Alkylations," *Bioorg. Med Chem.* 4(5):709–715, May 1996.

Ekins et al., "Examination of Purported Probes of Human CYP2B6," *Pharmacogenetics* 7(3):165–179, Jun. 1997.

Engel et al., "Prediction of CYP2D6–Mediated Polymorphic Drug Metabolism (Sparteine type) Based on in Vitro Investigations," *J. Chromatography B: Biomedical Applications* 678(1):93–103, Mar. 29, 1996.

Evans et al., "Pharmacogenomics: Translating Functional Genomics into Rational Therapeutics," *Science* 286(5439):487–491, Oct. 15, 1999.

Flanagan et al., "A Cytosine Analog that Confers Enhanced Potency to Antisense Oligonucleotides," *Proc. Natl. Acad. Sci. USA* 96(7):3513–3518, Mar. 30, 1999.

Forrester et al., "Evidence for Involvement of Multiple Forms of Cytochrome P–450 in Aflatocin $B_1$ Metabolism in Human Liver," *Proc. Natl. Acad. Sci. USA* 87(21):8306–8310, Nov. 1990.

Galfrè et al., "Preparation of Monoclonal Antibodies: Strategies and Procedures," *Methods Enzymol.* 37(Pt B):3–46, 1981.

Gayle et al., "Identification of Regions in Interleukin–1 α Important for Activity," *J Biol Chem.* 268(29):22105–22111, Oct. 15, 1993.

Giordano, "Intracoronary Gene Transfer of Fibroblast Growth Factor–5 Increases Blood Flow and Contractile Function in an Ischemic Region of the Heart," *Nat. Med.* 2(5):534–539, May 1996.

Gossen et al., "Tight Control of Gene Expression in Mammalian Cells by Tetracycline–Responsive Promoters," *Proc. Natl. Acad. Sci. USA* 89(12):5547–5551, Jun. 15, 1992.

Hashimoto et al., "Gene Structure of CYP3A4, an Adult–Specific Form of Cythochrome P450 in Human Livers, and its Transcriptional Control," *Eur J Biochem.* 218(2):585–595, Dec. 1, 1993.

Hawley et al., "Comparison of Binding of N3'→P5' Phosphoramidate and Phosphorothioate Oligonucleotides to Cell Surface Proteins of Cultured Cells," *Antisense & Nucleic Acid Drug Dev.* 9(1):61–69, Feb. 1999.

He et al., "Identification of Three Key Residues in Substrate Recognition Site 5 of Human Cytochrome P450 3A4 by Cassette and Site–Directed Mutagenesis," *Biochemistry* 36(29):8831–8839, Jul. 22, 1997.

Henry et al., "Reducing Liver Cancer—Global Control of Aflatoxin," *Science* 286(5449):2453–2454, Dec. 24, 1999.

Heyn et al., "Catalytic Role of Cytochrome P4502B6 in the N–Demethylation of S–Mephenytoin," *Drug Metab. & Dispos.* 24(9):948–954, Sep. 1996.

Hoffman et al., "Rapid Protein Structure Classification using One–Dimensional Structure Profiles on the BioSCAN Parallel Computer," *CABIOS* 11(6):675–679, Dec. 1995.

Inoue et al., "Assingment of the Human Cytochrome P–450 Nifedipine Oxidase Gene (CYP3A4) to Chromosome 7 at Band q22.1 by Fluorescence in situ Hybridization," *Jpn. J. Human Genet.* 37(2):133–138, Jun. 1992.

Isner et al., "Clinical Evidence of Angiogenesis After Arterial Gene Transfer of $phVEGF_{165}$ in Patient with Ischaemic Limb," *The Lancet* 348(9024):370–374, Aug. 10, 1996.

Jeanmougin et al., "Multiple Sequence Alignment with Clustal X," *TIBS* 23(10):403–405, Oct. 1998.

Jounaïdi et al., "Sequence of the 5'–Flanking Region of CYP3A5: Comparative Analysis with CYP3A4 and CYP3A7," *Biochem. Biophys. Res. Commun.* 205(3):1741–1747, Dec. 30, 1994.

Jounaïdi, "Detection of CYP3A5 Allelic Variant: a Candidate for the Polymorphic Expression of the Protein?," *Biochem. Biophys. Res. Commun.* 221(2):466–470, Apr. 16, 1996.

Kliewer et al., "An Orphan Nuclear Receptor Activated by Pregnanes Defines a Novel Steroid Signaling Pathway," *Cell* 92(1):73–82, Jan. 9, 1998.

Kobayashi et al., "Role of Human CYP2B6 in S–Mephobarbital N–Demethylation," *Drug Metab. Dispos.* 27(12):1429–1433, Dec. 1999.

Köhler et al., "Continuous Cultures of Fused Cells Secreting Antibody of Predefined Specificity," *Nature* 256(5517):495–497, Aug. 7, 1975.

Kumar et al., "Potent Inhibition of the Cytochrome P–450 3A–Mediated Human Liver Microsomal Metabolism of a Novel HIV Protease Inhibitor by Ritonavir: A Positive Drug–Drug Interaction," *Drug Metab. Dispos.* 27(8):902–908, Aug. 1998.

Le Mouellic et al., "Targeted Replacement of the Homeobox Gene *Hox–3.1* by the *Escherichia coli LacZ* in Mouse Chimeric Embryos," *Proc. Natl. Acad. Sci. USA* 87(12):4712–4716, Jun. 1990.

Lehmann et al., "The Human Orphan Nuclear Receptor PXR is Activated by Compounds that Regulate CYP3A4 Gene Expression and Cause Drug Interactions," *J Clin Invest.* 102(5):1016–1023, Sep. 1, 1998.

Li et al., "Substrates of Human Hepatic Cytochrome P450 3A4," *Toxicology* 104(1–3):1–8, Dec. 15, 1995.

Malmborg et al., "BIAcore as a Tool in Antibody Engineering," *J. Immunol. Methods* 183(1):7–13, Jun. 14, 1995.

Marshall, "Getting the Right Drug Into the Right Patient," *Nature Biotechnol.* 15(12):1249–1252, Nov. 1997.

Marshall, "Laying the Foundations for Personalized Medicines," *Nature Biotechnol.* 15(10):954–957, Oct. 1997.

Meyer, "Molecular Mechanisms of Genetic Polymorphisms of Drug Metabolism," *Annu. Rev. Pharmacol. Toxicol.* 37:269–296, 1997.

Meyer, "Overview of Enzymes of Drug Metabolism," *J. Pharmacokinetics Biopharm.* 24(5):449–459, Oct. 1996.

Monge et al., "Computer Modeling of Protein Folding: Conformational and Energetic Analysis of Reduced and Detailed Protein Models," i *J. Mol. Biol.* 247(5):995–1012, Apr. 14, 1995.

Mühlhauser et al., "VEGF$_{165}$ Expressed by a Replication–Deficient Recombinant Adenovirus Vector Induces Angiogenesis In Vivo," *Circ. Res.* 77(6):1077–1086, Dec. 1995.

Ohmori et al., "Steroid Hydroxylation by Human Fetal CYP3A7 and Human NADPH–Cytochrome P450 Reductase Coexpressed in Insect Cells Using Baculovirus," *Res. Commun. Mol. Pathol. Pharmacol.* 100(1):15–28, Apr. 1998.

Olszewski et al., "Folding Simulations and Computer Redesign of Protein A Three–Helix Bundle Motifs," *Proteins: Structure, Function and Genetics* 25(3):286–299, Jul. 1996.

Ostresh et al., "Generation and Use of Nonsupport–Bound Peptide and Peptidomimetic Combinatorial Libraries," *Methods Enzymol.* 267:220–234, 1996.

Ozawa, "Strategic Proposals for Avoiding Toxic Interactions with Drugs for Clinical Use During Development and After Marketing of a New Drug—Proposals for Designing Non–Clinical Studies—Is the Non–Clinical Study Useful?," *J. Toxicol. Sci.* 21(5):323–329, Dec. 1996.

Pabo et al., "Computer–Aided Model–Building Strategies for Protein Design," *Biochemistry* 25(20):5987–5991, Oct. 7, 1986.

Paolini et al., "Co–Carcinogenic Effect of β–Carotene," *Nature* 398(6730):760–761, Apr. 29, 1999.

Peng Ho et al., "Modification of Phosphorothioate Oligonucleotides Yields Potent Analogs with Minimal Toxicity for Antisense Experiments in the CNS," *Molecular Brain Research* 62(1):1–11, Nov. 12, 1998.

Peyronneau et al., "Expression in Yeast of Three Allelic cDNAs Coding for Human Liver P–450 3A4. Different Stabilities, Binding Properties and Catalytic Activities of the Yeast–Produced Enzymes," *Eur. J. Biochem.* 218(2):355–361, Dec. 1, 1993.

Rebbeck et al., "Modification of Clinical Presentation of Prostate Tumors by a Novel Genetic Variant in CYP3A4," *J. Natl. Cancer Inst.* 90(16):1225–1229, Aug. 19, 1998.

Renouf et al., "Molecular Modelling of Glycoproteins by Homology with Non–Glycosylated Protein Domains, Computer Simulated Glycosylation and Molecular Dynamics," *Adv. Exp. Med. Biol.* 376:37–45, 1995.

Rogers et al., "Amino Acid Sequences Common to Rapidly Degraded Proteins: the PEST Hypothesis," *Science* 234(4774):364–368, Oct. 17, 1986.

Ron et al., "Expression of Biologically Active Recombinant Keratinocyte Growth Factor. Structure/Function Analysis of Amino–Terminal Truncation Mutants," *J. Biol. Chem.* 268(4):2984–2988. Feb. 5, 1993.

Rose et al, "Three–Dimensional Structures of HIV–1 and SIV Protease Product Complexes," *Biochemistry* 35(39):12933–12944, Oct. 1, 1996.

Rutenber et al., "A New Class of HIV–1 Protease Inhibitor: the Crystallographic Structure, Inhibition and Chemical Systhesis of an Aminimide Peptide Isostere," *Bioorg. & Med. Chem.* 4(9):1545–1558, Sep. 1996.

Schaper et al., "Molecular Mechanisms of Coronary Collateral Vessel Growth," *Circ. Res.* 79(5):911–919, Nov. 1996.

Schaper et al., "Therapeutic Targets in Cardiovascular Disorders," *Curr. Opin. Biotechnol.* 7(6):635–640, Dec. 1996.

Schuetz et al., "Selective Expression of Cytochrome P450 CYP3A mRNAs in Embryonic and Adult Human Liver," *Pharmacogenetics* 4(1):11–20, Feb. 1994.

Shimada et al., "Interindividual Variations in Human Liver Cytochrome P–450 Enzymes Involved in the Oxidation of Drugs, Carcinogens and Toxic Chemicals: Studies with Liver Microsomes of 30 Japanese and 30 Caucasians," *J. Pharmacol. Exp. Ther.* 270(1):414–423, Jul. 1994.

Shoji et al., "Cellular Uptake and Biological Effects of Antisense Oligodeoxynucleotide Analogs Targeted to Herpes Simplex Virus," *Antimicrob. Agents Chemotherapy* 40(7):1670–1675, Jul. 1996.

Spiller et al., "The Influence of Target Protein Half–Life on the Effectiveness of Antisense Oligonucleotide Analog–Mediated Biologic Responses," *Antisense& Nucleic Acid Drug Dev.* 8(4):281–293, Aug. 1998.

Thummel et al., "In Vitro and In Vivo Drug Interactions Involving Human CYP3A," *Annu. Rev. Pharmacol. Toxicol.* 38:389–430, 1998.

Touw, "Clinical Implications of Genetic Polymorphisms and Drug Interactions Mediated by Cytochrome P–450 Enzymes," *Drug Metabolism and Drug Interactions* 14(2):55–82, 1997.

Wang et al., "Inhibitory Anti–CYP3A4 Peptide Antibody: Mapping of Inhibitory Epitope and Specificity Toward other CYP3A Isoforms," *Drug Metabolism and Disposition* 27(2):167–172, Feb. 1999.

Wang et al., "Second–Generation Adenovirus Vectors," *Nature Medicine* 2(6):714–716, Jun. 1996.

Wang et al., "Structure–Function Relationships of Human Liver Cytochromes P450 3A: Aflatoxin B1 Metabolism as a Probe," *Biochemistry* 37(36):12536–12545, Sep. 8, 1998.

West et al., "Interpatient Variability: Genetic Predisposition and Other Genetics Factors," *J. Clin. Pharmacol.* 37(7):635–648, Jul. 1997.

Westlind et al., "Interindividual Differences in Hepatic Expression of CYP3A4: Relationship to Genetic Polymorphism in the 5'–Upstream Regulatory Region," *Biochem. Biophys. Res. Commun.* 259(1):201–205, May. 27, 1999.

Williams et al., "Introduction of Foreign Genes into Tissues of Living Mice by DNA–Coated Miroprojectiles," *Proc. Natl. Acad. Sci. USA* 88(7):2726–2730, Apr. 1, 1991.

Witters et al., "Antisense Oligonucleotides to the Epidermal Growth Factor Receptor," *Breast Cancer Res. Treat.* 53(1):41–50, Jan. 1999.

Wodak, "Computer–Aided Design in Protein Engineering," *Annals N. Y. Acad. Sci.* 501:1–13, 1987.

Wolff et al., "Monoclonal Antibody Homodimers: Enhanced Antitumor Activity in Nude Mice," *Cancer Res.* 53(11):2560–2565, Jun. 1, 1993.

Yamazaki et al., "Procarcinogen Activation by Cytochrome P450 3A4 and 3A5 Expressed in *Escherichia Coli* and by Human Liver Microsomes," *Carcinogenesis* 16(9):2167–2170, Sep. 1995.

Yanev et al., "Selective Mechanism–Based Inactivation of Cytochromes P–450 2B1 and P–450 2B6 by a Series of Xanthates," *Drug Metab Dispos.* 27(5):600–604, May 1999.

Zhang et al., "Pharmacokinetics and Tissue Disposition of a Chimeric Oligodeoxynucleoside Phosphorothioate in Rats After Intravenous Administration," *J Pharmacol. Exp. Ther.* 278(2):971–979, Aug. 1996.

\* cited by examiner

FIG. 2

```
cyp3a4  ACT GCTGTGCAGG GCAGGAAAGC TCCATGCACA TAGCCCAGCA AAGAGCAACA CAGAGCTGAA AGGAAGACTC AGAGGAGAGA GATAAGTAAG GAAAGTAGTG ATG  106
cyp3a7  ........... .......... ...CA..... C......... .C...G.... .GCT..... .AA....... .......... .....G.... .......... ...   106
cyp3a5  ........G.. ......G... ...G...A.. C......... .C...G.... .TC..A.... .......... C..A.C.C.. T.G.AG.... .......G.C ...   105
cyp3ax  ..C T...G...A -A.AC..... ..T..ATG.. C......... ........G. .......C.. ..A.A..... ...A.C.... .C.G.AA... A....C.G.. ...   106
```

FIG. 3A

```
aagcagtggtaacaacgcagagcacgcgggGACCTCTGGGCAGAGAAACAAAGCT      25
CTATATGCACAGCCCAGCAAAGAGCAGCACACAGCTGAAAGAAAAACTCAGAAGA      80
CAGAGCTGAAAAAGAAAACTGGTGATG GAT CTC ATT CCA AAC TTT GCC     128
                             M   D   L   I   P   N   F   A
ATG GAA ACA TGG GTT CTT GTG GCT ACC AGC CTG GTA CTC CTC     170
 M   E   T   W   V   L   V   A   T   S   L   V   L   L
TAT ATT TAT GGG ACC CAT TCA CAT AAA CTT TTT AAG AAG CTG     212
 Y   I   Y   G   T   H   S   H   K   L   F   K   K   L
GGA ATT CCT GGG CCA ACC CCT CTG CCT TTT CTG GGA ACT ATT     254
 G   I   P   G   P   T   P   L   P   F   L   G   T   I
TTG TTC TAC CTT AGG GGT CTT TGG AAT TTT GAC AGA GAA TGT     296
 L   F   Y   L   R   G   L   W   N   F   D   R   E   C
AAT GAA AAA TAC GGA GAA ATG TGG GGG CTG TAT GAG GGG CAA     338
 N   E   K   Y   G   E   M   W   G   L   Y   E   G   Q
CAG CCC ATG CTG GTC ATC ATG GAT CCC GAC ATG ATC AAA ACA     380
 Q   P   M   L   V   I   M   D   P   D   M   I   K   T
GTG TTA GTG AAA GAA TGT TAC TCT GTC TTC ACA AAC CAG ATG     422
 V   L   V   K   E   C   Y   S   V   F   T   N   Q   M
CCT TTA GGT CCA ATG GGA TTT CTG AAA AGT GCC TTA AGT TTT     464
 P   L   G   P   M   G   F   L   K   S   A   L   S   F
GCT GAA GAT GAA GAA TGG AAG AGA ATA CGA ACA TTG CTA TCT     506
 A   E   D   E   E   W   K   R   I   R   T   L   L   S
CCA GCT TTC ACC AGT GTA AAA TTC AAG GAA ATG GTC CCC ATC     548
 P   A   F   T   S   V   K   F   K   E   M   V   P   I
ATT TCC CAA TGT GGA GAT ATG TTG GTG AGA AGC CTG AGG CAG     590
 I   S   Q   C   G   D   M   L   V   R   S   L   R   Q
GAA GCA GAG AAC AGC AAG TCC ATC AAC TTG AAA GAT TTC TTT     632
 E   A   E   N   S   K   S   I   N   L   K   D   F   F
GGG GCC TAC ACC ATG GAT GTA ATC ACT GGC ACA TTA TTT GGA     674
 G   A   Y   T   M   D   V   I   T   G   T   L   F   G
GTG AAC TTG GAT TCT CTC AAC AAT CCA CAA GAT CCC TTT CTG     716
 V   N   L   D   S   L   N   N   P   Q   D   P   F   L
AAA AAT ATG AAG AAG CTT TTA AAA TTG GAT TTT TTG GAT CCC     758
 K   N   M   K   K   L   L   K   L   D   F   L   D   P
TTT TTA CTC TTA ATA TCA CTC TTT CCA TTT CTT ACC CCA GTT     800
 F   L   L   L   I   S   L   F   P   F   L   T   P   V
TTT GAA GCC CTA AAT ATC GGT TTG TTT CCA AAA GAT GTT ACC     842
 F   E   A   L   N   I   G   L   F   P   K   D   V   T
CAT TTT TTA AAA AAT TCC ATT GAA AGG ATG AAA GAA AGT CGC     884
 H   F   L   K   N   S   I   E   R   M   K   E   S   R
CTC AAA GAT AAA CAA AAG CAT CGA GTA GAT TTC TTT CAA CAG     926
 L   K   D   K   Q   K   H   R   V   D   F   F   Q   Q
ATG ATC GAC TCC CAG AAT TCC AAA GAA ACA AAG TCC CAT AAA     968
 M   I   D   S   Q   N   S   K   E   T   K   S   H   K
GCT CTG TCT GAT CTG GAG CTT GTG GCC CAG TCA ATT ATC ATC    1010
 A   L   S   D   L   E   L   V   A   Q   S   I   I   I
ATT TTT GCT GCC TAT GAC ACA ACT AGC ACC ACT CTC CCC TTC    1052
 I   F   A   A   Y   D   T   T   S   T   T   L   P   F
ATT ATG TAT GAA CTG GCC ACT CAC CCT GAT GTC CAG CAG AAA    1094
 I   M   Y   E   L   A   T   H   P   D   V   Q   Q   K
CTG CAG GAG GAG ATT GAC GCA GTT TTA CCC AAT AAG GCA CCT    1136
```

FIG. 3B

```
 L   Q   E   E   I   D   A   V   L   P   N   K   A   P
GTC ACC TAC GAT GCC CTG GTA CAG ATG GAG TAC CTT GAC ATG 1178
 V   T   Y   D   A   L   V   Q   M   E   Y   L   D   M
GTG GTG AAT GAA ACG CTC AGA TTA TTC CCA GTT GTT AGT AGA 1220
 V   V   N   E   T   L   R   L   F   P   V   V   S   R
GTT ACG AGA GTC TGC AAG AAA GAT ATT GAA ATC AAT GGA GTG 1262
 V   T   R   V   C   K   K   D   I   E   I   N   G   V
TTC ATT CCC AAA GGG TTA GCA GTG ATG GTT CCA ATC TAT GCT 1304
 F   I   P   K   G   L   A   V   M   V   P   I   Y   A
CTT CAC CAT GAC CCA AAG TAC TGG ACA GAG CCT GAG AAG TTC 1346
 L   H   H   D   P   K   Y   W   T   E   P   E   K   F
TGC CCT GAA AGG TTC AGT AAG AAG AAC AAG GAC AGC ATA GAT 1388
 C   P   E   R   F   S   K   K   N   K   D   S   I   D
CTT TAC AGA TAC ATA CCT TTT GGA GCT GGA CCC CGA AAC TGC 1430
 L   Y   R   Y   I   P   F   G   A   G   P   R   N   C
ATT GGC ATG AGG TTT GCT CTC ACA AAC ATA AAA CTT GCT GTC 1472
 I   G   M   R   F   A   L   T   N   I   K   L   A   V
ATT AGA GCA CTG CAG AAC TTC TCC TTC AAA CCT TGT AAA GAG 1514
 I   R   A   L   Q   N   F   S   F   K   P   C   K   E
ACT CAG ATC CCA CTG AAA TTA GAC AAT CTA CCA ATT CTT CAA 1556
 T   Q   I   P   L   K   L   D   N   L   P   I   L   Q
CCA GAA AAA CCT ATT GTT CTA AAA GTG CAC TTA AGA GAT GGG 1598
 P   E   K   P   I   V   L   K   V   H   L   R   D   G
ATT ACA AGT GGA CCC TGACTTTCCCTAAGGACTTCCACTTTgttcaagaa 1639
 I   T   S   G   P   *
agctgtatccc
```

IDENTIFICATION OF A NEW MEMBER OF THE CYTOCHROME P450 3A (CYP3A) GENE FAMILY: CYP3AX

TECHNICAL FIELD

The present invention relates to the cytochrome P-450 (CYP) family of heme proteins, which mediate metabolic processes. More specifically, the present invention relates to polynucleotides encoding a novel CYP family member, the CYP3AX protein, and variants thereof. Further, the present invention relates to methods for identifying and obtaining drug candidates and inhibitors for therapy of disorders related to the malfunction of CYP3AX encoding genes, as well as to methods of diagnosing the status of such disorders.

BACKGROUND OF THE INVENTION

Members of the cytochrome P-450 (CYP) family of hemoproteins metabolize a wide variety of endogenous substrates and xenobiotics including carcinogens, toxins and drugs (Daly, *Toxicol. Lett.* 102–103 (1998), 143–7; Touw, *Drug Metabol. Drug Interact.* 14 (1997), 55–82). Of the human CYP proteins, members of the CYP3A subfamily are of major importance, since collectively they form the largest portion of all human CYP isoforms. The human CYP3A subfamily consists of three homologous proteins encoded by distinct genes (CYP3A4, CYP3A5 and CYP3A7) (Thummel, *Annu. Rev. Pharmacol. Toxicol.* 38 (1998), 389–430). The pharmacological significance of CYP3A is due to its expression in all major organs contributing to drug disposition (gastrointestinal tract, liver, kidney) and to its remarkably broad substrate spectrum. Based on the available experimental data it is estimated that between 45% and 60% of currently used drugs are substrates for CYP3A (Li, *Toxicology* 104 (1995), 1–8; Evans, *Science* 286 (1999), 487–91). The substrates of CYP3A include substances as diverse as steroids, antidepressants, benzodiazepines, immunosuppressive agents, imidazole antimycotics, macrolide antibiotics and toxins. The high homology among the CYP3A proteins and the available experimental data have led to the assumption that the three CYP3A isoforms have similar substrate spectra; however, some studies indicate the possibility of differences (Thummel, *Annu. Rev. Pharmacol. Toxicol.* 38 (1998), 389–430).

A considerable variation in the content and catalytic activity of CYP3A has been described in the general population. For example, the activities of the CYP3A4 protein in liver biopsies often vary up to 40-fold (Westlind, *Biochem. Biophys. Res. Commun.* 259 (1999), 201–5; Shimada, *J. Pharmacol. Exp. Ther.* 270 (1994), 414–23). Human in vivo studies have also indicated considerable interindividual variability in CYP3A4 activity, but its extent has been smaller. The reason for this discrepancy is not clear, but it could reflect the poor CYP3A isozyme specificity of the substrates used (Thummel, *Annu. Rev. Pharmacol. Toxicol.* 38 (1998), 389–430). CYP3A5 exhibits a similar variability of expression. In adult Caucasians, the CYP3A5 mRNA and protein were detected in the liver of 10 to 30% of samples, while the protein was found in the kidney and intestine of 70% subjects (Jounaidi, *Biochem. Biophys. Res. Commun.* 221 (1996), 466–70) and references therein). CYP3A7, the third CYP3A isoform, was originally isolated from fetal liver, and was subsequently found in 54% of liver samples in adults (Schuetz, *Pharmacogenetics* 4 (1994), 11–20).

The variability of CYP3A expression, coupled with the broad spectrum of drugs that are metabolized by CYP3A proteins, creates a potential for potentially harmful drug interactions involving these isozymes in patients undergoing therapies with multiple drugs (Thummel, *Annu. Rev. Pharmacol. Toxicol.* 38 (1998), 389–430). In addition, the interindividual variation in the CYP3A activity could also influence the individual predisposition to cancers caused by environmental carcinogens. For example, CYP3A proteins metabolize aflatoxin B1 (Wang, *Biochemistry* 37 (1998), 12536–45), a mycotoxin strongly implicated in the etiology of liver cancer, which is a major cause of premature death in many areas of Africa and Asia (Henry, *Science* 286 (1999), 2453–4). Forrester et al. (*Proc. Natl. Acad. Sci. U S A* 87 (1990), 8306–10) found that the rates of metabolic activation of aflatoxin B1 correlated with the level of CYP3A proteins in microsomes. It has also been proposed that high levels of CYP3A in humans could predispose an individual to cancer risk from bioactivated tobacco-smoke procarcinogens (Paolini, *Nature* 398 (1999), 760–1).

Clearly, there is a need for a better understanding of the factors underlying the variability of CYP3A expression and its effects on drug metabolism and drug efficacy. Such improved understanding of CYP3A family member structure, function and expression should lead to an optimization of therapies with drugs, for example in cancer treatment. The present invention fulfills this need and provides other related advantages.

SUMMARY OF THE INVENTION

It is an aspect of the present invention to provide a polynucleotide encoding a cytochrome P450 (CYP) 3AX polypeptide or a biologically active fragment thereof, that is (a) a polynucleotide encoding a polypeptide comprising the amino acid sequence depicted in SEQ ID NO: 2, 4, 6, 8 10 or 12; (b) a polynucleotide encoding a polypeptide, the polynucleotide comprising a coding sequence as depicted in any one of SEQ ID NOS: 1, 3, 5, 7, 9 or 11; (c) a polynucleotide encoding a polypeptide derived from the polypeptide encoded by a polynucleotide of (a) or (b) by way of substitution, deletion or addition of one or more amino acids of the amino acid sequence encoded by the polynucleotide of (a) or (b); (d) a polynucleotide the complementary strand of which hybridizes under moderately stringent conditions with a polynucleotide of any one of (a) to (c); (e) a polynucleotide encoding a polypeptide the sequence of which has an identity of at least 80% to the amino acid sequence of the polypeptide encoded by a polynucleotide of any one of (a) to (d); (f) a polynucleotide encoding a fragment or an epitope-bearing portion of a polypeptide encoded by a polynucleotide of any one of (a) to (e); (g) a polynucleotide encoding an epitope-bearing portion of a CYP3AX polypeptide comprising amino acid residues from about 405 to about 425 in SEQ ID NO: 2; (h) a polynucleotide comprising at least 15 nucleotides of a polynucleotide of any one of (a) to (g); (i) a polynucleotide of any one of (a) to (d), wherein at least one nucleotide is deleted, added or substituted and wherein the nucleotide deletion, substitution and/or addition results in an altered expression or activity of the CYP3AX polypeptide; (j) a polynucleotide encoding a molecular variant of the polypeptide encoded by the polynucleotide of (a) or (b); (k) a polynucleotide of (j), wherein the methionine at position 275 in SEQ ID NO. 2 is mutated; (l) a polynucleotide encoding a polypeptide that is immunospecifically recognized by an antibody that has been elicited by immunization with a polypeptide encoded by a polynucleotide of (a) or (b); (m) a polynucleotide which hybridizes under stringent conditions with a probe having the sequence of the polynucleotide of (a) or (b), or a fragment thereof; or (n) a polynucleotide the nucleotide sequence of which is a variant of the nucleotide sequence of a polynucleotide of any one of (a) to (m), due to genetic code degeneracy, or a complementary sequence thereto; provided that the polynucleotide does not consist of the nucleotide sequence set forth in SEQ ID NO: 35, SEQ ID NO: 36, SEQ ID NO: 37 or SEQ ID NO: 38.

In certain embodiments the polynucleotide is DNA, in certain embodiments it is genomic DNA and in certain embodiments it is RNA. In certain embodiments the polynucleotide is operatively linked to an expression control sequence. In certain other embodiments the invention relates to a vector comprising any one of the just described polynucleotides, and in certain other embodiments the invention relates to a host cell comprising any one of the just described polynucleotides or the just described vector.

It is another aspect of the invention to provide a method for producing a CYP3AX polypeptide or fragment thereof comprising (a) culturing the above described host cell under conditions and a time sufficient to permit expression of the polypeptide; and (b) isolating the protein or fragment from the culture. In other embodiments the invention provides a method for producing cells capable of expressing the CYP3AX polypeptide comprising genetically engineering cells with the any one of the just described polynucleotides or the just described vector.

In other embodiments the invention provides a CYP3AX protein or fragment thereof that is a polypeptide encoded by any one of the above described polynucleotides, a polypeptide produced by the method just described, or a polypeptide expressed by cells produced according to the method just described. In another embodiment the invention provides a gene encoding the CYP3AX protein, an in another embodiment there is provided an antibody which binds specifically to the CYP3AX protein. In other embodiments the invention provides a nucleic acid molecule or a vector comprising a nucleic acid sequence that is complementary to any one of the above described polynucleotides, and in other embodiments there is provided a nucleic acid molecule capable of specifically recognizing and cleaving any one of the above described polynucleotides, or a vector comprising such a nucleic acid molecule.

Turning to another aspect of the invention, there is provided a transgenic non-human animal comprising at least one of the above described polynucleotides, vectors or genes. In certain further embodiments, the animal comprises at least one inactivated wild type allele of the CYP3AX gene. In certain embodiments, the animal is a mouse or a rat.

In still another aspect, the invention provides a method of identifying and obtaining a CYP3AX inhibitor or activator capable of modulating the activity of the CYP3AX gene or the gene product thereof comprising the steps of (a) contacting the CYP3AX protein described above or a cell expressing the CYP3AX gene described above or comprising any one of the above described polynucleotides in the presence of components capable of providing a detectable signal in response to drug metabolism, with a compound to be screened under conditions that permit CYP3AX-mediated drug metabolism, and (b) detecting the presence or absence of a signal or increase of a signal generated from the metabolized drug, wherein the presence or increase of the signal is indicative for a putative inhibitor or activator. Thus, in particular embodiments the invention provides a method of identifying and obtaining a CYP3AX inhibitor or activator capable of modulating the activity of a CYP3AX gene or a gene product thereof, comprising the steps of: (a) contacting, in the presence of at least one component capable of providing a detectable signal in response to drug metabolism, either (i) the CYP3AX protein described above, or (ii) a cell expressing a CYP3AX gene or comprising a CYP3AX polynucleotide described above, in the absence and presence of a candidate compound under conditions and for a time sufficient to permit CYP3AX-mediated drug metabolism; and (b) comparing a level of the detectable signal provided in the absence of the agent to a level of the detectable signal provided in the presence of the agent, wherein an altered (i.e., increased or decreased in a statistically significant manner) signal level is indicative of an inhibitor or activator of a CYP3AX gene or of a CYP3AX gene product. In certain further embodiments the cell is a host cell as described above, or a CYP3AX producing cell obtained by the above described method, or is present in the transgenic non-human animal described above.

In another embodiment there is provided a method of identifying and obtaining an CYP3AX inhibitor or activator capable of modulating the activity of the CYP3AX gene or the gene product thereof comprising the steps of (a) contacting the CYP3AX protein of claim 10 with a first molecule known to be bound by the protein to form a first complex of the protein and the first molecule; (b) contacting the first complex with a candidate compound to be screened; and (c) measuring whether the compound displaces the first molecule from the first complex. In one embodiment, the measuring step comprises measuring the formation of a second complex of the protein and the compound, and in certain further embodiments the measuring step comprises measuring the amount of the first molecule that is not bound to the protein. In certain further embodiments the first molecule is cyclosporin, midazolam, lovastatin, nifedipin, diltiazem, erythromycin, lidocaine, amiodarone, or taxol. In other further embodiments, the first molecule is detectably labeled.

The present invention also provides a method for identifying a molecular variant of CYP3AX comprising (a) determining the presence or the level of any one of the above described polynucleotides in a sample from a subject; (b) determining the presence or the level of a CYP3AX protein; and (c) determining the presence of a mutation in the polynucleotide. In one embodiment the invention provides a method for identifying a molecular variant of CYP3AX comprising determining, in a sample from a subject, a level selected from the group consisting of (a) a level of the CYP3AX polynucleotide described above; (b) a level of a CYP3AX protein or fragment thereof as also described above; and (c) a level of the presence of a mutation in at least one of the above described CYP3AX polynucleotides. In a further embodiment the invention provides a method for diagnosing or prognosing a disorder related to the expression of a molecular variant CYP3AX gene, or susceptibility to such a disorder comprising the step of determining the level of drug metabolism. In certain embodiments the disorder is cancer. In certain other embodiments the method comprises PCR, ligase chain reaction, restriction digestion, direct sequencing, nucleic acid amplification techniques, hybridization techniques or immunoassays.

In certain other embodiments there is provided a method for identifying a molecular variant of CYP3AX comprising determining, in a sample from a subject, (a) a level of the CYP3AX polynucleotide described above; (b) a level of a CYP3AX protein or fragment thereof as described above; or (c) a level of the presence of a mutation in the CYP3AX polynucleotide described above. In a related embodiment there is provided a method for determining, in a subject, a risk for having or being susceptible to, the presence of, or the prognosis of a disorder related to the expression of a molecular variant CYP3AX gene, comprising the steps of determining, in a sample from the subject, (1) a level of drug metabolism; and (2) a level selected from the group consisting of (a) a level of the CYP3AX polynucleotide described above; (b) a level of a CYP3AX protein or fragment thereof described above; and (c) a level of the presence of a mutation in the CYP3AX polynucleotide described above. In certain further embodiments, said disorder is cancer. In certain other further embodiments, at least one level is determined by PCR, ligase chain reaction, restriction nuclease digestion, direct nucleotide sequencing, a nucleic acid amplification technique, a nucleic acid hybridization technique or an immunoassay. In another embodiment there is provided a method for treating a disorder related to the expression of a molecular variant CYP3AX gene in a subject, comprising (a) identifying the disorder according to any one of the methods just described; and (b) administering to the subject a medicament to abolish or alleviate said disorder, where the selection and dosage of such medicament will be known to a person having ordinary skill in the art based upon the disclosure herein.

In certain other embodiments the method further comprises administering to a subject a medicament to abolish or alleviate the disorder. In certain other further embodiments there is provided a method for the production of a pharmaceutical composition comprising synthesizing the compound identified and obtained in the method or a derivative thereof in a pharmaceutically acceptable form. In another further embodiment the method comprises formulating a drug or pro-drug in the form suitable for therapeutic application and preventing or ameliorating the disorder of the subject diagnosed in the just described methods. In a further embodiment the compound drug or prodrug is a derivative of a medicament administered as described above. In another embodiment the invention relates to an inhibitor or activator identified or obtainable by any of the above described methods. In a further embodiment the inhibitor or activator binds specifically to the above described CYP3AX protein.

Turning to another embodiment, the invention provides a method for the detection of any one of the above described CYP3AX polynucleotides, or a method for genotyping of individual CYP3AX alleles or variants. In certain embodiments, the polynucleotide is a CYP3AX polynucleotide as described above or a complementary nucleic acid molecule thereto or a ribozyme. In one embodiment the oligonucleotide is about 15 to 50 nucleotides in length, which in certain further embodiments is an oligonucleotide. In another embodiment the invention provides a method of detecting a CYP3AX protein comprising detection of a CYP3AX binding antibody as described above, detection of a CYP3AX binding protein, detection of the expression of a CYP3AX gene comprising a CYP3AX polynucleotide or detection of a CYP3AX allelic variant. In certain further embodiments, the method of detecting a CYP3AX protein further comprises distinguishing two or more CYP3AX alleles or variants.

In other embodiments the invention is directed to the use of an effective dose of a drug or prodrug for the preparation of a pharmaceutical composition for the treatment or prevention of a disorder of a subject comprising a CYP3AX polynucleotide, wherein in certain further embodiments the disorder is cancer.

BRIEF DESCRIPTION OF THE DRAWINGS

FIG. 2 shows sequence comparison of 5' portions of CYP3A transcripts as determined by 5'-RACE. The "ATG" in bold represents the codon encoding initiating methionine in all proteins. Dots indicate sequence identities.

FIGS. 3A and 3B shows a 1639 bp CYP3AX cDNA sequence and the deduced translated CYP3AX amino acid sequence as determined by 5'-RACE and RT-PCR. Nucleotides shown in small caps represent the oligonucleotides used for 5'-RACE and RT-PCR, respectively. Arrowheads indicate exon boundaries of the gene

Figure 1:
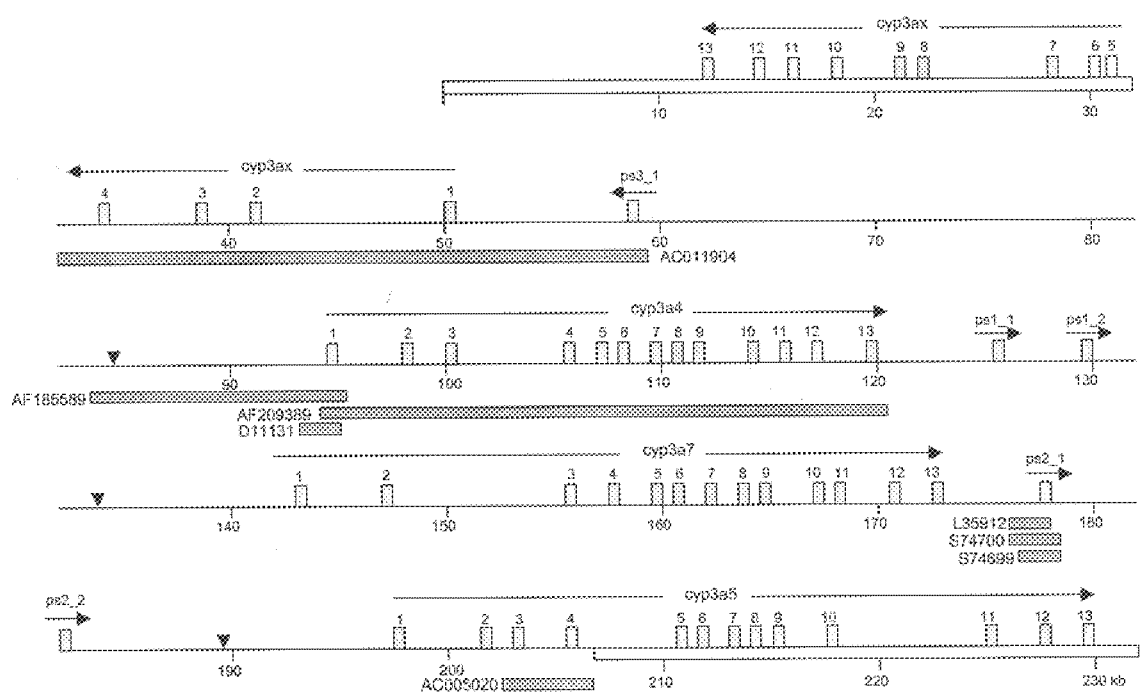
FIG. 1 shows genomic organization of the human CYP3A locus. The sequence derived from BAC 22300 is depicted as a line, the sequences derived from BAC clones AC011904 and AC005020 as empty horizontal bars, the overlap between the three BAC clones as light-shaded bars. Dark-shaded bars with accession numbers attached represent CYP3A genomic sequences deposited in the GenBank. Horizontal arrows indicate orientations of the open reading frames. Arrowheads indicate duplication boundaries within the locus.

Several documents are cited throughout the text of this specification. Each of the documents cited herein (including any manufacturer's specifications, instructions, etc.) is hereby incorporated herein by reference as if set forth in its entirety; however, there is no admission that any document cited is indeed prior art as to the present invention.

DETAILED DESCRIPTION OF THE INVENTION

The present invention is based on the finding of a novel cytochrome p450 3A gene family member, named CYP3AX. The identification of this novel gene should contribute to a better understanding of the regulation and variabilities in CYP3A activity among individuals.

The elucidation of genetic factors that control inducibility and activity of CYP3A proteins or genes in a patient allows the optimization of therapies with CYP3A substrates, and also permits the identification of subpopulations with increased risk of developing several common cancers. These and related advantages of the present invention may be useful in the determination of an individual's predisposition to several common cancers, including, for example and according to non-limiting theory, those caused by environmental carcinogens.

In a first embodiment, the invention provides polynucleotides encoding CYP3AX, oligonucleotides useful for detecting a CYP3AX gene, and embodiments related thereto such as vectors, host cells, variant CYP3AX proteins and methods for producing the same.

In yet another embodiment, the invention provides methods for identifying and obtaining drug candidates and inhibitors of CYP3AX for therapy of disorders related to acquired drug hypo- or hypersensitivity, as well as methods of diagnosing the status of such disorders.

In a further embodiment, the invention provides pharmaceutical and diagnostic compositions comprising the above-described CYP3AX polynucleotides, oligonucleotides, vectors, proteins, antibodies thereto, and drugs and inhibitors obtainable by the above-described method.

The pharmaceutical and diagnostic compositions, methods and uses of the invention are useful for the diagnosis and treatment of cancer and other diseases the therapy of which may at least in part depend on drug treatment and tolerance. The novel variant forms of CYP3AX genes according to the invention provide compositions and methods for the development of a pharmacodynamic profile of drugs for a given patient.

The variability of CYP3A expression plays an important role in individual drug bioavailability and inefficacy of drug therapy. The variability of CYP3A activity is assumed to reflect the combined effect of modulation by environmental or therapeutical chemicals and of thus far unidentified genetic factors. With respect to modulation, several distinct mechanisms lead to an inhibition of CYP3A proteins which may be transient, intermediate or irreversible (Thummel, *Annu. Rev. Pharmacol. Toxicol.* 38 (1998), 389–430). In addition, many common drugs such as glucocorticoids (e.g., dexamethasone), antibiotics (e.g., rifampicin) and antimycotics (e.g., clotrimazole) increase the expression levels of CYP3A and the extent of this phenomenon is individually variable. The induction of CYP3A is the result of transcriptional activation (Thummel, *Annu. Rev. Pharmacol. Toxicol.* 38 (1998), 389–430). Recently, a number of studies have led to the identification of a human orphan nuclear receptor, the pregnane X receptor (hPXR) as a major activator of CYP3A transcription (Kliewer, *Cell* 92 (1998), 73–82; Lehmann, *J. Clin. Invest.* 102 (1998), 1016–23; Bertilsson, *Proc. Natl. Acad. Sci. USA* 95 (1998), 12208–13). HPXR undergoes activation by the known CYP3A inducers and the resulting transcriptional activation of CYP3A involves the formation of a dimer with the retinoid X receptor (RXR).

A significant portion of the interindividual variability is thought to be caused by genetic factors which are largely unknown.

To establish a basis for a search for genetic variance in CYP3A genes the sequence of the human CYP3A locus has been determined and analyzed. Surprisingly, a novel, fourth member of the CYP3A gene family has been identified. The gene encodes for a protein with between 71.5% and 75.8% identity to the other CYP3A proteins and it is expressed predominantly in the liver and in the testes. Transcript analysis has revealed the presence of several splice variants. The characterization of the full CYP3A locus and the surprising identification of a new member of the family should add to efforts to dissect the genetic variants underlying its variable expression. This should lead to a better optimization of therapies with the numerous substrates of the CYP3A family.

The terms "gene", "polynucleotide", "nucleic acid sequence", "nucleotide sequence", "DNA sequence" or "nucleic acid molecule" as used herein refer to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. Preferably, the polynucleotide of the invention comprises a coding sequence encoding at least the mature form of the above defined protein, i.e., the protein which is posttranslationally processed in its biologically active form, for example due to cleavage of leader or secretory sequences or a proprotein sequence or other natural proteolytic cleavage points. Also included are splice variants of the polynucleotide of SEQ ID NO: 1, for example as described below, in Table 1 or in SEQ ID NOS: 3, 5, 7, 9 or 11.

The polynucleotide which encodes at least the predicted mature polypeptide of the protein comprising SEQ ID NO: 2 or for a fragment thereof may include: only the coding sequence for the mature polypeptide and additional coding sequence such as a leader or secretory sequence or a proprotein sequence or the coding sequence for the mature polypeptide (and optionally additional coding sequence) and non-coding sequence, such as intron or non-coding sequence 5' and/or 3' of the coding sequence for the predicted mature polypeptide.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances. Thus, the nucleotide sequences of the present invention can be engineered in order to alter the protein coding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns, to change codon preference, to produce splice variants, etc.

By "CYP3AX polypeptide" polypeptides are meant that exhibit activity similar, but not necessarily identical, to an activity of the wild-type CYP3AX protein of the invention or an activity that is enhanced or reduced over that of the wild-type proteins (either the full-length protein or, preferably, the mature protein), as measured in a particular biological assay. The activity of CYP3AX can be determined using expression systems and assays previously developed for the other members of the family. These include expression in bacteria (He, *Biochemistry* 36 (1997), 8831–9), in the baculovirus (Wang, *Drug Metab. Dispos.* 27 (1999), 167–72; Ohmori, *Res. Commun. Mol. Pathol. Pharmacol.* 100 (1998), 15–28), and in mammalian cells (Crespi, *Pharm. Res.* 13 (1996), 1635–41). These assays can be used to measure the level of activity of partially purified or purified native or recombinant protein.

The term "epitope-bearing portion" of a protein according to the invention denotes proteins or peptides which have at least a part of the primary structural conformation for one or more epitopes capable of reacting specifically with antibodies to a protein which is encodable by a nucleic acid molecule as set forth above. Preferably, the peptides and proteins encoded by a polynucleotide of the invention are recognized by an antibody that specifically recognizes an epitope comprising the amino acid residues that are unique for the protein. Preferably, the peptides and proteins are capable of eliciting an effective immune response in a mammal, for example mouse or rabbit.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)). An example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Suitable moderately stringent conditions include, for example, prewashing in a solution of 5 ×SSC, 0.5% SDS, 1.0 mM EDTA (pH 8.0); hybridizing at 50° C.–70° C., 5 × SSC for 1–16 hours; followed by washing once or twice at 22–65° C. for 20–40 minutes with one or more each of 2×, 0.5× and 0.2× SSC containing 0.05–0.1% SDS. For additional stringency, conditions may include a wash in 0.1× SSC and 0.1% SDS at 50–60° C. for 15–40 minutes. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

Transcription activating proteins derived from other organisms, preferably other plants, in particular cereals, may be encoded by other DNA sequences which hybridize to the sequences for transcription activating proteins under relaxed hybridization conditions and which code on expression for peptides having the ability to activate transcription. Examples of such non-stringent hybridization conditions are 4×SSC at 50° C. or hybridization with 30–40% formamide at 42° C. Such molecules comprise those which are fragments, analogues or derivatives of the transcription activating protein of the invention and differ, for example, by way of amino acid and/or nucleotide deletion(s), insertion(s), substitution(s), addition(s) and/or recombination(s) or any other modification(s) known in the art either alone or in combination from the above-described amino acid sequences or their underlying nucleotide sequence(s). Using the PESTFIND program (Rogers, *Science* 234 (1986), 364–368), PEST sequences (rich in proline, glutamic acid, serine, and threonine) can be identified, which are characteristically present in unstable proteins. Such sequences may be removed from the proteins in order to increase their stability and optionally the activity of the proteins. Methods for introducing such modifications in the nucleic acid molecules according to the invention are well-known to the person skilled in the art.

Also provided in the present invention are species homologs of CYP3AX. Species homologs may be isolated and identified by making suitable probes or primers from the sequences provided herein and screening a suitable nucleic acid source for the desired homologue.

Thus, by the provision of the nucleotide sequence of SEQ ID NO: 1 as well as those encoding the amino acid sequence depicted in SEQ ID NO: 2, it is possible to isolate identical or similar nucleic acid molecules which encode CYP3AX proteins from other species or organisms, in particular orthologous CYP3AX genes from mammals other than human. The term "orthologous" as used herein refers to homologous genes of different species that arose from a common ancestor during evolution. Orthologous genes may or may not be responsible for a similar function; see, e.g., the glossary of the "Trends Guide to Bioinformatics", Trends Supplement 1998, Elsevier Science.

In certain preferred embodiments, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In the context of the present invention the term "molecular variant" CYP3AX gene or protein as used herein means that the CYP3AX gene or protein differs from the wild type CYP3AX gene or protein by way of nucleotide substitution(s), addition(s) and/or deletion(s). The term "molecular variants" further relates to genetic polymorphisms in the CYP3AX gene. Such mutations in the gene, in particular in the coding region of the gene can be expected to cosegregate and optionally lead to altered biochemical properties of the CYP3AX protein such as protein stability, activity or substrate specificity and will lead to interindividual differences in drug metabolisms. The identification of genetic polymorphisms in the CYP3AX gene is described in the examples. In particular, it was found that methionine 275 has been mutated to isoleucine. "Molecular variant" refers to a polynucleotide or polypeptide differing from the CYP3AX polynucleotide or polypeptide, but retaining some essential properties thereof such as the immunological activity. Generally, variants are overall closely similar, and, in many regions, identical to the CYP3AX polynucleotide or polypeptide or are highly homologous to the nucleic acid molecules.

Homology is understood to refer to a sequence identity of at least 80%, preferably at least 85%, more preferably more than 90% and still more preferably more than 95%. The deviations from the sequences of the nucleic acid molecules described above can, for example, be the result of nucleotide substitution(s), deletion(s), addition(s), insertion(s) and/or recombination(s); see supra. Homology can further imply that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other mammals, or mutations. These mutations may occur naturally or may be obtained by mutagenesis techniques. The allelic variations may be naturally occurring allelic variants as well as synthetically produced or genetically engineered variants; see supra.

The polynucleotide of the present invention comprise those which encode fragments, analogues or derivatives and in particular orthologues of the above-described CYP3AX proteins and differ, for example, by way of amino acid and/or nucleotide deletion(s), insertion(s), substitution(s), addition(s) and/or recombination(s) or any other modification(s) known in the art either alone or in combination from the above-described amino acid sequences or their underlying nucleotide sequence(s). Methods for introducing such modifications in the nucleic acid molecules according to the invention are well-known to the person skilled in the art. All such fragments, analogues and derivatives of the protein of the invention are included within the scope of the present invention, as long as the essential characteristic immunological and/or biological properties as defined herein remain unaffected in kind.

However, many polynucleotide sequences, such as EST sequences, are publicly available and are accessible through sequence databases. Some of these sequences are related to SEQ ID NO: 1 and may have been publicly available prior to conception of the present invention. Preferably, such related polynucleotides are specifically excluded from the scope of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the CYP3AX polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO: 1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6 (1990), 237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identify are: Matrix= Unitary, k-tuple=4, Mismatch Penalty=1, Joining Penalty= 30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/ aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino, acid residues in the subject sequence may be inserted, deleted, added or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequences shown in SEQ ID NO: 2 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6 (1990), 237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The CYP3AX variants may contain alterations in the coding regions, non-coding regions, or both. Polynucleotide variants can be produced for a variety of reasons. e.g., to optimize codon expression for a particular host (change codons in the human mRNA to those preferred by a bacterial host such as E. coli).

Naturally occurring CYP3AX variants are called "allelic variants," and refer to one of several alternate forms of a gene occupying a given locus on a chromosome of an organism. (Genes II, Lewin, B., ed., John Wiley & Sons, New York (1985) and updated versions). These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the CYP3AX polypeptides. For instance, one or more amino acids can be deleted from the N-terminus or C-terminus of the protein without substantial loss of biological function. The authors of Ron, J. Biol. Chem. 268 (1993), 2984–2988, reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli, J. Biotechnology 7 (1988), 199–216).

Moreover, ample evidence demonstrates that variants often retain a biological activity similar to that of the naturally occurring protein. For example, Gayle and coworkers (J. Biol. Chem. 268 (1993); 22105–22111) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]"; see Abstract. In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art. Furthermore, using the PESTFIND program (Rogers, Science 234 (1986), 364–368), PEST sequences (rich in proline, glutamic acid, serine, and threonine) can be identified, which are characteristically present in unstable proteins. Such sequences may be removed from the CYP3AX proteins in order to increase the stability and optionally the activity of the proteins. Methods for introducing such modifications in the nucleic acid molecules according to the invention are well-known to the person skilled in the art.

By comparing amino acid sequences in different species, conserved amino acids can be identified. These conserved amino acids are likely important for protein function. In contrast, the amino acid positions where substitutions have been tolerated by natural selection indicates that these positions are not critical for protein function.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244 (1989), 1081–1085) The resulting mutant molecules can then be tested for biological activity.

Conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The polynucleotide of the invention may be, e.g., DNA, cDNA, genomic DNA, RNA or synthetically produced DNA or RNA or a recombinantly produced chimeric nucleic acid molecule comprising any of those polynucleotides either alone or in combination.

Preferably said polynucleotide is part of a vector, particularly plasmids, cosmids, viruses and bacteriophages used conventionally in genetic engineering that comprise a polynucleotide of the invention. Such vectors may comprise further genes such as marker genes which allow for the selection of said vector in a suitable host cell and under suitable conditions.

In a further preferred embodiment of the vector or the polynucleotide of the invention, the polynucleotide of the invention is operatively linked to expression control sequences allowing expression in prokaryotic or eukaryotic cells. Expression of said polynucleotide comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli,* and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (in-vitrogene), pSPORT1 (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The present invention furthermore relates to host cells transformed with a polynucleotide or vector of the invention. Said host cell may be a prokaryotic or eukaryotic cell; see supra. The polynucleotide or vector of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination; see for example Mouellic, *Proc. Natl. Acad. Sci. USA,* 87 (1990), 4712–4716; Joyner, *Gene Targeting, A Practical Approach,* Oxford University Press.

The host cell can be any prokaryotic or eukaryotic cell, such as a bacterial, insect, fungal, plant, animal or human cell. Preferred fungal cells are, for example, those of the genus Saccharomyces, in particular those of the species *S. cerevisiae*. The term "prokaryotic" is meant to include all bacteria which can be transformed or transfected with a polynucleotide for the expression of a CYP3AX polypeptide or fragment thereof. Prokaryotic hosts may include gram negative as well as gram positive bacteria such as, for example, *E. coli, S. typhimurium, Serratia marcescens* and *Bacillus subtilis*. A polynucleotide coding for the CYP3AX polypeptide or mutant form of CYP3AX polypeptides can be used to transform or transfect the host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of the polypeptide of the present invention in, e.g., prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The proteins of the invention can then be isolated from the grown medium, cellular lysates, or cellular membrane fractions. The isolation and purification of the microbially or otherwise expressed polypeptides of the invention may be by any conventional means such as for example, preparative chromatographic separations and immunological separations such as those involving the use of monoclonal or polyclonal antibodies.

Thus, in a further embodiment the invention relates to a method for the production of the polypeptide of the present invention and fragments thereof comprising culturing a host cell as defined above under conditions allowing the expression of the protein and recovering the produced protein or fragment from the culture.

In another embodiment the present invention relates to a method for producing cells capable of expressing a CYP3AX polypeptide comprising genetically engineering cells with the polynucleotide or with the vector of the invention. The cells obtainable by the method of the invention can be used, for example, to test drugs according to the methods described in Sambrook, Fritsch, Maniatis (1989). Molecular cloning: a laboratory manual. Cold Spring Harbour Laboratory press, Cold Spring Harbour; Peyronneau, *Eur. J Biochem.* 218 (1993), 355–61; Yamazaki, *Carcinogenesis* 16 (1995), 2167–2170. Furthermore, the cells can be used to study known drugs and unknown derivatives thereof for their ability to complement loss of drug efficacy caused by mutations in the CYP3AX gene. For these embodiments the host cells preferably lack a wild type allele, preferably both alleles of the CYP3AX gene and/or have at least one mutated from thereof. Alternatively, strong overexpression of a mutated allele over the normal allele and comparison with a recombinant cell line overexpressing the normal allele at a similar level may be used as a screening and analysis system. The cells obtainable by the above-described method may also be used for the screening methods referred to herein below.

Furthermore, the invention relates to CYP3AX proteins and fragments thereof encoded by a polynucleotide according to the invention or obtainable by the above-described methods or from cells produced by the method described above. In this context it is also understood that the CYP3AX protein according to the invention may be further modified by conventional methods known in the art. By providing the CYP3AX protein according to the present invention it is also possible to determine the portion(s) relevant for its biological activity or inhibition of the same. It is understood that all forms of the CYP3AX protein are encompassed by the term "CYP3AX polypeptide", "polypeptide" or "protein".

The invention also provides polypeptides having one or more amino acids deleted from both the amino and/or the carboxyl termini.

Also preferred are CYP3AX polypeptide fragments characterized by structural or functional domains. Preferred embodiments of the invention include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions, substrate binding region, and high antigenic index regions. As set out in the Figures, such preferred regions include Garnier-Robson alpharegions, beta-regions, turn-regions, and coil-regions, Chou-Fasman alpha-regions, beta-regions, and turn-regions, Kyte-Doolittle hydrophilic regions and hydrophobic regions, Eisenberg alpha and beta amphipathic regions, Karplus-Schulz flexible regions, Emini surface-forming regions, and Jameson-Wolf high antigenic index regions.

Other preferred fragments are biologically or immunologically active CYP3AX fragments. Biologically active fragments are those exhibiting activity similar, but not necessarily identical, to an activity of the CYP3AX polypeptide. The biological activity of the fragments may include an improved desired activity, or a decreased undesirable activity. Biological activity as provided herein thus may include, for example by way of illustration and not limitation, immunological activities such as immunogenicity (e.g., the ability to elicit an immune response) or antigenicity (e.g., the ability to be recognized by an immune system component), pharmacological activities, metabolic activities, physiologic and respiratory activities, enzymatic and/or signal transduction activities including, for example, apoptotic activities, or any other structural or functional biological criterion by which CYP3AX or a derived fragment therefrom may exhibit a particular activity.

The present invention also relates to a gene encoding the protein of the present invention. The gene structure of CYP3AX was initially investigated using the cDNA and gene structure information from the homologous gene CYP3A4 (Hashimoto, *Eur. J. Biochem.* 218 (1993), 585–95). The results of the analysis indicated that, similarly to the other CYP3A genes, CYP3AX consists of 13 exons. All the presumptive intron/exon junctions have the canonical splice sites (not shown). Transcribed "in silico". the resulting open reading frame encompasses 1509 nucleotides, beginning with a methionine-coding codon ATG and it is followed by a consensus "stop" codon (TGA) (FIG. 3). The corresponding putative protein consists of 503 amino acids with a calculated molecular weight of 57669 daltons. A sequence comparison reveals between 71.5% and 75.8% identity between the putative CYP3AX protein and the other members of the CYP3A subfamily (Table 3).

Figure 4:
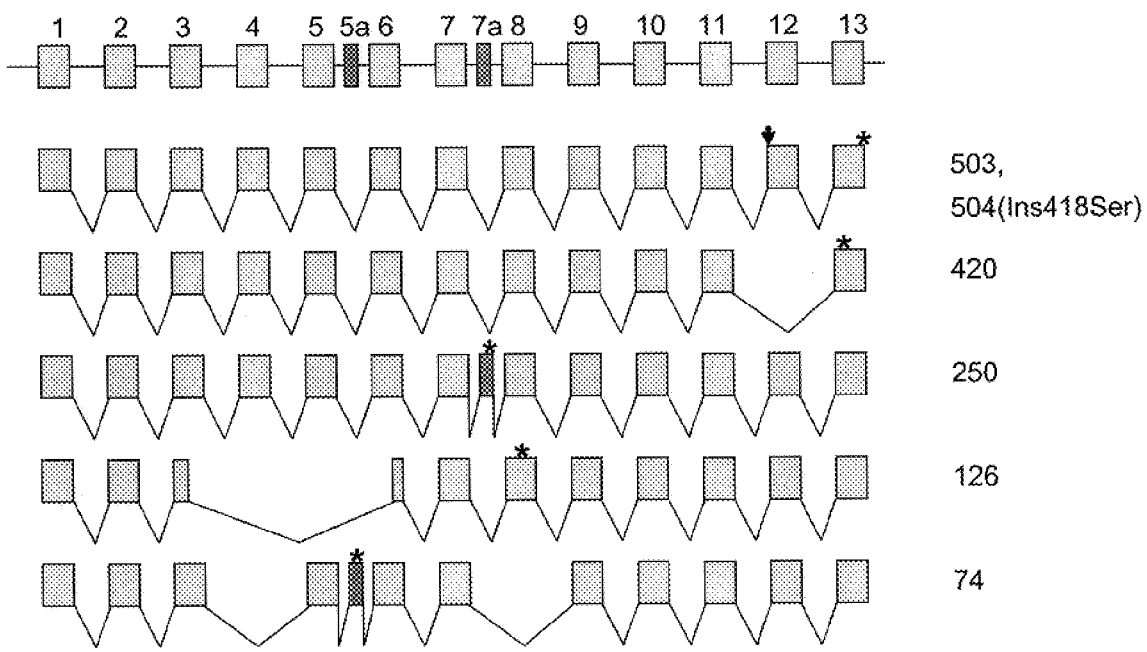
FIG. 4 depicts a schematic representation of the alternative and aberrant splicing of CYP3AX gene transcripts. Light-shaded boxes indicate the canonical (exonic), dark-shaded boxes the aberrant (intronic), portions of the transcript. Genomic elements found in CYP3AX transcripts are summarized in the uppermost part of the figure.

CYP3AX is expressed as several different transcripts, apparently due to alternative as well as defective gene splicing (FIG. 4). The two transcripts with the highest structural similarity to the other members of the human CYP3A family contain open reading frames encoding 503 or 504 acids, respectively. The difference is consistent with the alternate utilization of two consensus splice sites on the 5' boundary of exon 12. The usage of the more 5' site results in the inclusion in the transcript of a trinucleotide which in consequence leads to the insertion of an additional serine residue at position 418 of the putative protein encoded by the "504(Ins418Ser)" variant (SEQ ID NO: 3). The other four CYP3AX transcripts contain open reading frames which translate to putative polypeptides of 420, 250, 126 and 74 amino acids, respectively (FIG. 4). The "420" variant arises through splicing out of the exon 12 of the gene with the resulting shift and premature termination of the open reading frame (SEQ ID NO. 5). The premature termination of the "250" variant is due to the aberrant splicing of intron 7 (SEQ ID NO. 7). The "126" variant results from a shift of the reading frame caused by the aberrant splicing of 3' and 5' portions of exons 3 and 6, respectively with the consequential deletion of exons 4 and 5 (SEQ ID NO. 9). The "74" transcript arises through the removal of exons 4 and 8 as well as through the aberrant splicing of intron 5 (SEQ ID NO. 11).

The present invention furthermore relates to antibodies specifically recognizing the CYP3AX protein according to the invention. Advantageously, the antibody specifically recognizes a wildtype CYP3AX protein or a variant CYP3AX protein.

Antibodies against the protein of the invention can be prepared by well known methods using a purified protein according to the invention or a (synthetic) fragment derived therefrom as an antigen. Monoclonal antibodies can be prepared, for example, by the techniques as originally described in Köhler and Milstein, *Nature* 256 (1975), 495, and Galfré,*Meth. Enzymol.* 73 (1981), 3, which comprise the fusion of mouse myeloma cells to spleen cells derived from immunized mammals. The antibodies can be monoclonal antibodies, polyclonal antibodies or synthetic antibodies as well as fragments of antibodies, such as Fab, Fv or scFv fragments etc. As used herein, an antibody is said to "specifically bind" or "immunospecifically recognize" a cognate antigen if it reacts at a detectable level with the antigen, but does not react detectably with peptides containing an unrelated sequence, or a sequence of a different heme protein. Thus, for example, an antibody is said to be "immunospecific" or to "specifically bind" a CYP3AX polypeptide if it reacts at a detectable level with CYP3AX, preferably with an affinity constant, Ka, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci. USA* 51:660 (1949)) or by surface plasmon resonance (BlAcore, Biosensor, Piscataway, N.J.). See, e.g., Wolff et al., *Cancer Res.* 53:2560–2565 (1993).

Furthermore, antibodies or fragments thereof to the aforementioned polypeptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of the CYP3AX protein of the invention as well as for the monitoring of the presence of such CYP3AX protein, for example, in transgenic organisms, and for the identification of compounds interacting with the proteins according to the invention. For example, surface plasmon resonance as employed in the BlAcore system can be used to increase the efficiency of phage antibodies which bind to an epitope of the protein of the invention (Schier, *Human Antibodies*

*Hybridomas* 7 (1996), 97∝105; Malmborg, *J. Immunol. Methods* 183 (1995), 7–13). Antibodies, which bind specifically to a wildtype or a variant protein can be used for diagnosing or prognosing a related disorder, e.g., cancer.

Furthermore, the present invention relates to nucleic acid molecules which represent or comprise the complementary strand of any of the above described polynucleotides or a part thereof. Such a molecule may either be a deoxyribonucleic acid or a ribonucleic acid. Such molecules comprise, for example, antisense RNA. These molecules may furthermore be linked to sequences which when transcribed code for a ribozyme thereby producing a ribozyme which specifically cleaves transcripts of polynucleotides according to the invention.

Furthermore, the present invention relates to a vector comprising a nucleic acid molecule according to the invention. Examples for such vectors are described above. Preferably, the nucleic acid molecule present in the vector is operatively linked to regulatory elements permitting expression in prokaryotic or eukaryotic host cells; see supra.

The invention also relates to transgenic non-human animals such as transgenic mouse, rats, hamsters, dogs, monkeys, rabbits, pigs, C. elegans and fish such as torpedo fish comprising a polynucleotide or vector of the invention or obtained by the method described above, preferably wherein said polynucleotide or vector is stably integrated into the genome of said non-human animal, preferably such that the presence of said polynucleotide or vector leads to the expression of the CYP3AX gene of the invention. It may have one or several copies of the same or different polynucleotides of the CYP3AX gene. This animal has numerous utilities, including as a research model for drug tolerability and therefore, presents a novel and valuable animal in the development of therapies, treatment, etc. for diseases caused by deficiency or failure of drug metabolism in the cell. Accordingly, in this instance, the mammal is preferably a laboratory animal such as a mouse or rat.

A method for the production of a transgenic non-human animal, preferably transgenic mouse, comprises introduction of a polynucleotide or vector of the invention into a germ cell, an embryonic cell, stem cell or an egg or a cell derived therefrom. The non-human animal can be used in accordance with the method of the invention described below and may be a non-transgenic healthy animal, or may have a disorder, for example a disorder caused by at least one mutation in the CYP3AX gene or an altered expression compared to the wildtype. Such transgenic animals are well suited for, e.g., pharmacological studies of drugs in connection with wildtype or variant forms of the above described CYP3AX proteins since these proteins or at least their functional domains are conserved between species in higher eukaryotes, particularly in mammals. Production of transgenic embryos and screening of those can be performed, e.g., as described by A. L. Joyner Ed., Gene Targeting, A Practical Approach (1993), Oxford University Press. The DNA of the embryos can be analyzed using, e.g., Southern blots with an appropriate probe.

Preferably, the transgenic non-human animal of the invention further comprises at least one inactivated wild type allele of the CYP3AX gene. This embodiment allows for example the study of the interaction of various variant forms of the CYP3AX protein. It might be also desirable to inactivate CYP3AX gene expression or function at a certain stage of development and/or life of the transgenic animal. This can be achieved by using, for example, tissue specific, developmental and/or cell regulated and/or inducible promoters which drive the expression of, e.g., an antisense or ribozyme directed against the RINA transcript of the CYP3AX gene; see also supra. A suitable inducible system is for example tetracycline-regulated gene expression as described, e.g., by Gossen and Bujard (*Proc. Natl. Acad. Sci.* 89 *USA* (1992), 5547–5551) and Gossen et al. (*Trends Biotech.* 12 (1994), 58–62).

With the CYP3AX polynucleotides or protein and its variants as well as the vector of the invention, it is now possible to study in vivo and in vitro the efficiency of drugs in relation to the activity of CYP3AX protein, or in relation to particular mutations in the CYP3AX gene of a patient and the affected phenotype. Furthermore, the CYP3AX protein of the invention can be used to determine the pharmacological profile of drugs and for the identification and preparation of further drugs which may be more effective for the treatment of, e.g., cancer, in particular for the amelioration of certain phenotypes caused by the respective mutations such as those described above.

Thus, a particular object of the present invention concerns drug/pro-drug selection and formulation of pharmaceutical compositions for the treatment of diseases which are amenable to chemotherapy taking into account a polymorphism of the CYP3AX gene that may cosegregate with the affected phenotype of the patient to be treated. This allows the safe and economic application of drugs which for example were hitherto considered not appropriate for therapy of, e.g., cancer due to either their side effects in some patients and/or their unreliable pharmacological profile with respect to the same or different phenotype(s) of the disease. The means and methods described herein can be used for example to improve dosing recommendations and allows the prescriber to anticipate necessary dose adjustments depending on the considered patient group.

In a further embodiment the present invention relates to a method of identifying and obtaining a CYP3AX inhibitor or activator capable of modulating the activity of the CYP3AX gene or its gene product comprising the steps of (a) contacting the protein of the invention or a cell expressing the gene of the present invention or comprising a polynucleotide of the invention in the presence of components capable of providing a detectable signal in response to drug metabolism, with a compound to be screened under conditions that permit CYP3AX mediated drug metabolism, and (b) detecting the presence or absence of a signal or increase of a signal generated from the metabolized drug, wherein the presence or increase of the signal is indicative for a putative inhibitor or activator.

The term "compound" in a method of the invention includes a single substance or a plurality of substances which may or may not be identical.

Said compound(s) may be chemically synthesized or produced via microbial fermentation but can also be comprised in, for example, samples, e.g., cell extracts from, e.g., plants, animals or microorganisms. Furthermore, said compounds may be known in the art but hitherto not known to be useful as an inhibitor, respectively. The plurality of compounds may be, e.g., added to the culture medium or injected into a cell or non-human animal of the invention.

If a sample containing (a) compound(s) is identified in the method of the invention, then it is either possible to isolate the compound from the original sample identified as containing the compound, in question or one can further subdivide the original sample, for example, if it consists of a plurality of different compounds, so as to reduce the number of different substances per sample and repeat the method with the subdivisions of the original sample. It can then be determined whether said sample or compound displays the desired properties, for example, by the methods described herein or in the literature (e.g., Yanev, *Drug Metab. Dispos.* 27 (1999), 600–604; Kobayashi, *Drug Metab. Dispos.* 27 (1999), 1429–1433; Kumar, *Drug. Metab. Dispos.* 27 (1999), 902–908; Ekins, *Pharmacogenetics* 7 (1997), 165–179; Heyn, *Drug Metab. Dispos.* 24 (1996), 948–954). Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art or by using and modifying the methods as described herein. Furthermore, the person skilled in the art will readily recognize which further compounds and/or enzymes may be used in order to perform the methods of the invention, for example, enzymes, if necessary, that convert a certain compound into the precursor which in turn represents a substrate for the CYP3AX protein. Such adaptation of the method of the invention is well within the skill of the person skilled in the art and can be performed without undue experimentation.

Suitable assays which can be employed in accordance with the present invention are described, for example, in Hashimoto, *Eur. J. Biochem.* 218 (1993), 585–95 wherein transfection assays with chimeric CYP3A4 genes in HepG2 cells are described. Similarly, the CYP3AX gene can be expressed or co-expressed in HepG2 cells and analyzed for its transcriptional activity and the catalytic properties of CYP3AX. Such an assay can also be used for studying the catalytic properties of the CYP3AX protein on its substrates such as cyclosporine, midazolam, lovastatin, nifedipin, diltiazem, erythromycin, lidocaine, amiodarone or taxol.

In particular, such tests are useful to add in predicting whether a given drug will interact in an individual carrying a variant CYP3AX gene. In addition heterologous expression systems such as yeast can be used in order to study the stability, binding properties and catalytic activities of the gene products of a variant CYP3AX genes compared to the corresponding wild type CYP3AX gene product. As mentioned before, the CYP3AX and the molecular variant CYP3AX gene and their gene products, particularly when employed in the above described methods, can be used for pharmacological and toxicological studies of the metabolism of drugs. Preferred drugs to be tested in accordance with the methods of the present invention are, e.g., cyclosporine, midazolam, lovastatin, nifedipin, diltiazem, erythromycin, lidocaine, amiodarone or taxol.

Compounds which can be used in accordance with the present invention include peptides, proteins, nucleic acids, antibodies, small organic compounds, ligands, peptidomimetics, PNAs and the like. Said compounds can also be functional derivatives or analogues of known drugs such as from those described above. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, said derivatives and analogues can be tested for their effects according to methods known in the art or as described. Furthermore, peptide mimetics and/or computer aided design of appropriate drug derivatives and analogues can be used, for example, according to the methods described below. Such analogs comprise molecules having as the basis structure of known CYP3AX-substrates and/or inhibitors and/or modulators; see infra.

Appropriate computer programs can be used for the identification of interactive sites of a putative inhibitor and the CYP3AX protein of the invention by computer assistant searches for complementary structural motifs (Fassina, *Inmunomethods* 5 (1994), 114–120). Further appropriate computer systems for the computer aided design of protein and peptides are described in the prior art, for example, in Berry, *Biochem. Soc. Trans.* 22 (1994), 1033–1036; Wodak, *Ann. N.Y. Acad. Sci.* 501 (1987), 1–13; Pabo, *Biochemistry* 25 (1986), 5987–5991. The results obtained from the above-described computer analysis can be used in combination with the method of the invention for, e.g., optimizing known inhibitors. Appropriate peptidomimetics and other inhibitors can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, *Methods in Enzymology* 267 (1996), 220–234 and Dorner, *Bioorg. Med. Chem.* 4 (1996), 709–715. Furthermore, the three-dimensional and/or crystallographic structure of inhibitors and the CYP3AX protein of the invention can be used for the design of peptidomimetic drugs (Rose, Biochemistry 35 (1996), 12933–12944; Rutenberg, *Bioorg. Med. Chem.* 4 (1996), 1545–1558).

In summary, the present invention provides methods for identifying and obtaining compounds which can be used in specific doses for the treatment of specific forms of diseases, e.g., cancer, the chemotherapy of which is complicated by malfunctions of the CYP3AX gene often resulting in an altered activity or level of drug metabolism or sensitive phenotype.

In a preferred embodiment of the method of the invention said cell is a cell of or obtained by the method of the invention or is comprised in the above-described transgenic non-human animal.

In a further embodiment the present invention relates to a method of identifying and obtaining an CYP3AX inhibitor or activator capable of modulating the activity of the CYP3AX gene or gene product thereof comprising the steps of (a) contacting the CYP3AX protein of the invention with a first molecule known to be bound by the protein to form a first complex of said protein and said first molecule;

(b) contacting said first complex with a candidate compound to be screened; and (c) measuring whether said compound displaces said first molecule from said first complex.

Advantageously, in said method said measuring step comprises measuring the formation of a second complex of said protein and said compound. Preferably, said measuring step comprises measuring the amount of said first molecule that is not bound to said protein.

In a particularly preferred embodiment of the above-described method said first molecule is for example cyclosporin, midazolam, lovastatin, nifedipin, diltiazem, erythromycin, lidocaine, amiodarone, or taxol. Furthermore, it is preferred that in the method of the invention said first molecule is labeled, e.g., with a radioactive or fluorescent label.

In a still further embodiment the present invention relates to a method for identifying a molecular variant of CYP3AX polynucleotide or its expression products comprising (a) determining the presence or the level of the polynucleotide of any one of claims 1 to 4 in a sample from a subject;

(b) determining the presence or the level of a protein of claim 10; and/or (c) determining the presence of a mutation in the polynucleotide of any one of claims 1 to 4.

The mRNA, cRNA, cDNA or genomic DNA obtained from the subject may be sequenced to identify mutations which may be characteristic fingerprints of mutations in the CYP3AX gene. The present invention further comprises methods wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments as described above.

Further modifications of the above-mentioned embodiment of the invention can be easily devised by the person skilled in the art, without any undue experimentation from this disclosure; see, e.g., the examples. An additional embodiment of the present invention relates to a method wherein said determination is effected by employing an antibody of the invention or fragment thereof. The antibody used in the method of the invention may be labeled with detectable tags such as a histidine flags or a biotin molecule.

In accordance with the present invention, the mode and population distribution of novel so far unidentified genetic variations in the CYP3AX gene can be analyzed by sequence analysis of relevant regions of the human CYP3AX gene from many different individuals. In particular mutations can exist in the coding regions of the gene that can be expected to cosegregate and optionally lead to altered biochemical properties of the CYP3AX protein such as protein stability, activity, or substrate specificity and will lead to interindividual differences in drug metabolism. It is a well known fact that genomic DNA of individuals, which harbor the individual genetic makeup of all genes, including CYP3AX can easily be purified from individual blood samples. These individual DNA samples are then used for the analysis of the sequence composition of the CYP3AX gene alleles that are present in the individual which provided the blood sample.

One important parameter that had to be considered in the attempt to determine the individual CYP3AX genotype and identify novel CYP3AX variants by direct DNA-sequencing of PCR-products from human blood genomic DNA is the fact that each human harbors (usually, with very few abnormal exceptions) two gene copies of each autosomal gene (diploidy). Because of that, great care had to be taken in the evaluation of the sequences to be able to identify unambiguously not only homozygous sequence variations but also heterozygous variations. The details of the different steps in the identification and characterization of novel CYP3AX gene polymorphisms (homozygous and heterozygous) are described in the literature.

The methods of the mutation analysis followed standard protocols and are described in detail in the examples. In general such methods to be used in accordance with the present invention for evaluating the phenotypic spectrum as well as the overlapping clinical characteristics with other forms of drug metabolism and altered tolerance to drugs in patients with mutations in the CYP3AX gene encompass for example haplotype analysis, single-strand conformation polymorphism analysis (SSCA), PCR and direct sequencing. On the basis of thorough clinical characterization of many patients the phenotypes can then be correlated to these mutations as well as to mutations that had been described earlier for other CYPs.

As is evident to the person skilled in the art this new molecular genetic knowledge can now be used to exactly characterize the genotype of the index patient where a given drug takes an unusual effect and of his family.

For the investigation of the nature of the alterations in the amino acid sequence of the CYP3AX proteins computer programs may be used such as BRASMOL that are obtainable from the Internet. Furthermore, folding simulations and computer redesign of structural motifs can be performed using other appropriate computer programs (Olszewski, *Proteins* 25 (1996), 286–299; Hoffman, *Comput. Appl. Biosci.* 11 (1995), 675–679). Computers can be used for the conformational and energetic analysis of detailed protein models (Monge, *J. Mol. Biol.* 247 (1995), 995–1012; Renouf, *Adv. Exp. Med. Biol.* 376 (1995), 37–45). These analysis can be used for the identification of the influence of a particular mutation on binding and/or metabolism of drugs.

A further embodiment relates to a method for diagnosing or prognosing of a disorder related to the expression of a molecular variant CYP3AX gene, or susceptibility to such a disorder comprising the steps of the method for identifying a molecular variant and further determining the level of drug metabolism.

Over the past 20 years, genetic heterogeneity has been increasingly recognized as a significant source of variation in drug response. Many scientific communications (Meyer, *Ann. Rev. Pharmacol. Toxicol.* 37 (1997), 269–296 and West, *J. Clin. Pharmacol.* 37 (1997), 635–648) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's (Marshall, *Nature Biotechnology,* 15 (1997), 954–957; Marshall, *Nature Biotechnology,* 15 (1997), 1249–1252). In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient, for example, and characterization of disease (Bertz, *Clin. Pharmacokinet.* 32 (1997), 210–256; Engel, *J. Chromatogra. B. Biomed. Appl.* 678 (1996), 93–103). For the providers of health care, such as health maintenance organizations in the US and government public health services in many European countries, this pharmacogenomics approach can represent a way of both improving health care and reducing overheads because there is a large cost to unnecessary therapies, ineffective drugs and drugs with side effects. Methods for determining drug metabolism are for example described in bacteria (He, *Biochemistry* 36 (1997), 8831–9), in the baculovirus (Wang, *Drug Metab. Dispos.* 27 (1999), 167–72; Ohmori, *Res. Commun. Mol. Pathol. Pharmacol.* 100 (1998), 15–28), and in mammalian cells (Crespi, *Pharm. Res.* 13 (1996), 1635–41).

Detection of the expression of a variant CYP3AX gene would allow the conclusion that said expression is interrelated to the generation or maintenance of a corresponding phenotype of the disease. Accordingly, a step would be applied to reduce the expression level to low levels or abolish the same. This can be done, for example, by at least partial elimination of the expression of the mutant gene by biological means, for example, by the use of ribozymes, antisense nucleic acid molecules, intracellular antibodies or the above described inhibitors against the variant forms of these CYP3AX proteins. Furthermore, pharmaceutical products may be developed that reduce the expression levels of the corresponding mutant proteins and genes or the expression of the wildtype gene might be altered, i.e., increased.

In accordance with this embodiment of the present invention, the method of testing the status of a disorder or susceptibility to such a disorder can be effected by using a polynucleotide or a nucleic acid molecule of the invention, e.g., in the form of a Southern or Northern blot or in situ analysis. Said nucleic acid sequence may hybridize to a coding region of either of the genes or to a non-coding region, e.g., intron. In the case that a complementary sequence is employed in the method of the invention, said nucleic acid molecule can again be used in Northern blots. Additionally, said testing can be done in conjunction with an actual blocking, e.g., of the transcription of the gene and thus is expected to have therapeutic relevance. Furthermore, a primer or oligonucleotide can also be used for hybridizing to one of the above-mentioned CYP3AX gene or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or level of expression of the CYP3AX gene can be monitored by using a primer pair that specifically hybridizes to either of the corresponding nucleic acid sequences and by carrying out a PCR reaction according to standard procedures. Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985.

In a preferred embodiment of the present invention, the above described methods comprise PCR, ligase chain reaction, restriction digestion, direct sequencing, nucleic acid amplification techniques, hybridization techniques or immunoassays (Sambrook et al., loc. cit. CSH cloning, Harlow and Lane loc. cit. CSH antibodies).

In a preferred embodiment of the method of the present invention said disorder is cancer, in particular liver or lung cancer.

In a further embodiment of the above-described method, a further step comprising administering to the subject a medicament to abolish or alleviate variations detected in the CYP3AX gene in accordance with all applications of the method of the invention allows treatment of a given disease before the onset of clinical symptoms due to the phenotype response caused by the CYP3AX gene.

In a preferred embodiment of the method of the invention said medicament are chemotherapeutic agents such as substrates of CYP3AX, e.g., cyclosporin, midazolam, lovastatin, nifedipin, diltiazem, erythromycin, lidocaine, amiodarone, or taxol.

In a further embodiment the invention relates to a method for the production of a pharmaceutical composition comprising the steps of any one of the above described methods and synthesizing and/or formulating the compound identified or a derivative or homologue thereof in a pharmaceutically acceptable form. The therapeutically useful compounds identified according to the method of the invention may be formulated and administered to a patient as discussed above. For uses and therapeutic doses determined to be appropriate by one skilled in the art see infra.

Furthermore, the present invention relates to a method for the preparation of a pharmaceutical composition comprising the steps of the above-described methods; and formulating a drug or pro-drug in the form suitable for therapeutic application and preventing or ameliorating the disorder of the subject diagnosed in the method of the invention. Drugs or pro-drugs after their in vivo administration are metabolized in order to be eliminated either by excretion or by metabolism to one or more active or inactive metabolites (Meyer, *J. Pharmacokinet. Biopharm.* 24 (1996), 449–459). Thus, rather than using the actual compound or inhibitor identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, *J. Toxicol. Sci.* 21 (1996), 323–329).

In a preferred embodiment of the method of the present invention said drug or prodrug is a derivative of a medicament as defined hereinbefore.

In a still further embodiment the present invention relates to an inhibitor identified or obtained by the method described hereinbefore. Preferably, the inhibitor binds specifically to the CYP3AX protein of the invention. The antibodies, nucleic acid molecules and inhibitors of the present invention preferably have a specificity at least substantially identical to the binding specificity of the natural ligand or binding partner of the CYP3AX protein of the invention. An antibody or inhibitor can have a binding affinity to the CYP3AX protein of the invention of at least $10^5$ $M^{-1}$, preferably higher than $10^7$ $M^{-1}$ and advantageously up to $10^{10}$ $M^{-1}$ in case CYP3AX activity should be repressed. Hence, in a preferred embodiment, a suppressive antibody or inhibitor of the invention has an affinity of at least about $10^{-7}$ M, preferably at least about $10^{-9}$ M and most preferably at last about $10^{-11}$ M.

Furthermore, the present invention relates to the use of an oligo- or polynucleotide for the detection of a polynucleotide of the invention and/or for genotyping of corresponding individual CYP3AX alleles. Preferably, said oligo- or polynucleotide is a polynucleotide or a nucleic acid molecule of the invention described before.

In a particular preferred embodiment said oligonucleotide is about 15 to 50, preferably 20 to 40, more preferably 20 to 30 nucleotides in length and comprises the nucleotide sequence of SEQ ID NO: 1 or a complementary sequence.

Hence, in a still further embodiment, the present invention relates to a primer or probe consisting of an oligonucleotide as defined above. In this context, the term "consisting of" means that the nucleotide sequence described above and employed for the primer or probe of the invention does not have any further nucleotide sequences of the CYP3AX gene immediately adjacent at its 5' and/or 3' end. However, other moieties such as labels, e.g., biotin molecules, histidine tags (e.g., polyhistidine "flags"), antibody fragments, colloidal gold, etc. as well as nucleotide sequences which do not correspond to the CYP3AX gene may be present in the primer and probes of the present invention. Furthermore, it is also possible to use the above described particular nucleotide sequences and to combine them with other nucleotide sequences derived from the CYP3AX gene wherein these additional nucleotide sequences are interspersed with moieties other than nucleic acids or wherein the nucleic acid does not correspond to nucleotide sequences of the CYP3AX gene. Furthermore, it is evident to the person skilled in the art that the oligonucleotide can be modified, for example, by thio-phosphate-backbones and/or base analogs well known in the art (Flanagan, *Proc. Natl. Acad. Sci. USA* 96 (1999), 3513–8; Witters, *Breast Cancer Res. Treat.* 53 (1999), 41–50; Hawley, *Antisense Nucleic Acid Drug Dev.* 9 (1999), 61–9; Peng Ho, *Brain Res. Mol. Brain Res.* 62 (1998), 1–11; Spiller, *Antisense Nucleic Acid Drug Dev.* 8 (1998), 281–93; Zhang, *J. Pharmacol. Exp. Ther.* 278 (1996), 971–9; Shoji, *Antimicrob. Agents Chemother.* 40 (1996), 1670–5; Crooke, *J. Pharmacol. Exp. Ther.* 277 (1996), 923–37).

In addition, the present invention relates to the use of an antibody or a substance capable of binding specifically to the gene product of a CYP3AX gene for the detection of the CYP3AX protein, the expression of CYP3AX gene, e.g., comprising a polynucleotide of the invention and/or for distinguishing CYP3AX alleles comprising a polynucleotide of the invention or its molecular variant.

Moreover, the present invention relates to a composition, preferably a pharmaceutical composition comprising the antibody, the nucleic acid molecule, the vector, the activator or the inhibitor of the present invention, and optionally a pharmaceutically acceptable carrier. These pharmaceutical compositions comprising, e.g., the inhibitor or pharmaceutically acceptable salts thereof may conveniently be administered by any of the routes conventionally used for drug administration, for instance, orally, topically, parenterally or by inhalation. Acceptable salts comprise acetate, methylester, HCl, sulfate, chloride and the like. The compounds may be administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Furthermore, the use of pharmaceutical compositions which comprise antisense-oligonucleotides which specifically hybridize to RNA encoding mutated versions of a CYP3AX gene or which comprise antibodies specifically recognizing mutated CYP3AX protein but not or not substantially the functional wild-type form is conceivable in cases in which the concentration of the mutated form in the cells should be reduced.

Thanks to the present invention the particular drug selection, dosage regimen and corresponding patients to be treated can be determined in accordance with the present invention. The dosing recommendations will be indicated in product labeling by allowing the prescriber to anticipate dose adjustments depending on the considered patient group, with information that avoids prescribing the wrong drug to the wrong patients at the wrong dose.

Furthermore, the present invention relates to a diagnostic composition or kit comprising any one of the aforedescribed polynucleotides, oligonucleotides, probes, vectors, host cells, proteins, antibodies, inhibitors, activators or nucleic acid molecules of the invention, and optionally suitable means for detection.

The kit of the invention may contain further ingredients such as selection markers and components for selective media suitable for the generation of transgenic cells and animals. The kit of the invention may advantageously be used for carrying out a method of the invention and could be, inter alia, employed in a variety of applications, e.g., in the diagnostic field or as research tool. The parts of the kit of the invention can be packaged individually in vials or in combination in containers or multicontainer units. Manufacture of the kit follows preferably standard procedures which are known to the person skilled in the art. The kit or diagnostic compositions may be used for methods for detecting expression of the CYP3AX gene in accordance with any one of the above-described methods of the invention, employing, for example, immunoassay techniques such as radioimmunoassay or enzymeimmunoassay or preferably nucleic acid hybridization and/or amplification techniques such as those described herein before and in the examples.

In another embodiment the present invention relates to the use of a drug or prodrug for the preparation of a pharmaceutical composition for the treatment or prevention of a disorder diagnosed by the method described hereinbefore.

Some genetic changes lead to altered protein conformational states. For example, some CYP3AX proteins may possess a tertiary structure that renders them far less capable of facilitating drug metabolism and transcription initiation, respectively. Restoring the normal or regulated conformation of mutated proteins is the most elegant and specific means to correct these molecular defects, although it is difficult. Pharmacological manipulations thus may aim at restoration of wild-type conformation of the protein. Thus, the polynucleotides and encoded proteins of the present invention may also be used to design and/or identify molecules which are capable of activating the wild-type function of a CYP3AX gene or protein.

Furthermore, the present invention relates to the use of an effective dose of a nucleic acid sequence encoding a functional and expressible CYP3AX protein for the preparation of a pharmaceutical composition for treating, preventing and/or delaying a disorder diagnosed by the method of the invention. A gene encoding a functional and expressible CYP3AX protein can be introduced into the cells which in turn produce the protein of interest.

As used throughout this specification, "functional" CYP3AX gene means a gene wherein the encoded protein having part or all of the primary structural conformation of the wild type CYP3AX protein, i.e., possessing the biological property of metabolizing drugs. This embodiment of the present invention is suited for therapy of, e.g., cancer in particular in humans. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, *Nature Medicine* 2 (1996), 534–539; Schaper, *Circ. Res.* 79 (1996), 911–919; Anderson, *Science* 256 (1992), 808–813; Isner, *Lancet* 348 (1996), 370–374; Muhlhauser, *Circ. Res.* 77 (1995), 1077–1086; Wang, *Nature Medicine* 2 (1996), 714–716; WO94/29469; WO 97/00957 or Schaper, Current Opinion in Biotechnology 7 (1996), 635–640, and references cited therein. The gene may be designed for direct introduction or for introduction via liposomes, or viral vectors (e.g., adenoviral, retroviral) into the cell. Preferably, said cell is a germ line cell, embryonic cell, or egg cell or derived therefrom, most preferably said cell is a stem cell.

As is evident from the above, it is preferred that in the use of the invention the nucleic acid sequence is operatively linked to regulatory elements allowing for the expression and/or targeting of the protein of the present invention to specific cells. Suitable gene delivery systems that can be employed in accordance with the invention may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (*Proc. Natl. Acad. Sci. USA* 88 (1991), 2726–2729). Standard methods for transfecting cells with recombinant DNA are well known to those skilled in the art of molecular biology, see, e.g., WO 94/29469; see also supra. Gene therapy may be carried out by directly administering the polynucleotide or vector of the invention to a patient or by transfecting cells with the polynucleotide or vector of the invention ex vivo and infusing the transfected cells into the patient.

In a preferred embodiment of the uses and methods of the invention, said disorder is cancer, in particular, cancer of the lung, breast and kidney, respectively.

The pharmaceutical and diagnostic compositions, uses, methods of the invention can be used for the diagnosis and treatment of all kinds of diseases hitherto unknown as being related to or dependent on CYP3AX gene. The compositions, methods and uses of the present invention may be desirably employed in humans, although animal treatment is also encompassed by the methods and uses described herein.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on Internet, e.g., under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research tools.html, http://www.tigr.org/, are known to the person skilled in the art and can also be obtained using, e.g., http://www.lycos.com. An overview of patent information in biotechnology and a survey of relevant sources of patent information useful for retrospective searching and for current awareness is given in Berks, *TIBTECH* 12 (1994), 352–364.

The invention will now be described by reference to the following examples which are merely illustrative and are not to be construed as a limitation of the scope of the present invention.

EXAMPLES

Example 1

BAC SEQUENCING AND SEQUENCE ASSEMBLY

A CYP3A4-containing bacterial artificial chromosome (BAC) (No. 22300) was isolated by Genome Systems from a human genomic BAC library using oligonucleotides derived from the promoter region of the gene. The oligonucleotide sequences were: CYP3A4PF 5'- AAC AGG CGT GGA AAC ACA AT-3' (SEQ ID NO. 13) and CYP3APR 5'-CTT TCC TGC CCT GCA CAG-3' (SEQ ID NO: 14) (Rebbeck, *J. Natl. Cancer Inst.* 90 (1998), 1225–9). Genomic fragments of app. 1400 bp were derived from BAC DNA by nebulization and subcloned into the pCR library vector (GATC GmbH, Konstanz, Germany). Nine hundred and sixty clones were picked for DNA isolation and sequencing in both directions using PerkinElmer capillary 3700 DNA analyzers. This was followed by three rounds of gap closing which involved direct sequencing of the BAC DNA as well as sequence editing.

Example 2

SEQUENCE ANALYSIS

The assembly of sequences derived from BAC subclones was performed using the Phred-Phrap-Consed package (University of Washington, Seattle, USA). Pairwise alignments, and translations of open reading frames were done with the STADEN program package (MRC Laboratory of Molecular Biology, Cambridge, UK). ClustalX (Jeanmougin, *Trends Biochem. Sci.* 23 (1998), 403–5) was used for multiple alignments of exon and intron sequences. Exon and STS mapping, identification and masking of genomic repeats and the determination of duplication boundaries were performed using the GEMS Launcher package (Genomatix, Munich, Germany).

Example 3

RNA ISOLATION, 5'-RACE AND RT-PCR

Total RNA was isolated from lysed hepatocytes and liver samples using the RNeasy kit (Qiagen, Hilden, Germany). For RT-PCR, cDNA pools were generated from 0.5 ug of total RNA using an oligo dT primer and Superscript reverse transcriptase (Life Technologies, Karlsruhe, Germany). The cDNA used for one semiquantitative RT-PCR was derived from 35 ng total RNA. Panels of cDNA derived from various human tissues were purchased from Clontech (Clontech MTC panels, catalogue numbers K1420-1, K1421-1, K1425-1). The primers used in expression and induction studies were: 3A4-105F 5'- ATA TGG AAC CCA TTC ACA TG-3' (SEQ ID NO: 15) and 3A4106R 5'-CAG GCT GTT GAC CAT CAT AAA AG-3' (SEQ ID NO: 16) (exons 2 and 4 of CYP3A4, respectively), 3AX-3F 5'- CTA TGA CAC AAC TAG CAC CAC-3' (SEQ ID NO: 17) and 3AX-4R 5'-CAT AGA TTG GAA CCA TCA CTG-3' (SEQ ID NO: 18)

(exons 10 and 11 of CYP3AX, respectively) and h-GAPDH-3F 5'-GGC TCT CCA GAA CAT CAT CCC TGC-3'(SEQ ID NO: 19) and h-GAPDH-4R 5'-GGG TGT CGC TGT TGA AGT CAG AGG-3'(SEQ ID NO: 20). Primers 3AX-67F and 3AX-64R (exons 1 and 13, respectively) were used to amplify the open reading frame of CYP3AX as well as its splice variants. 5'rapid amplification of cDNA (5'-RACE) was performed using the SMART RACE cDNA Amplification Kit (Clontech), according to the manufacturer's instructions. The gene-specific oligonucleotides were 3AX-63R 5'-GAG GAG TAC CAG GCT GGT AGC CAC A-3' (SEQ ID NO: 21), 3A4-109R 5'-GCA CAG GCT GTT GAC CAT CAT AAA AG-3' (SEQ ID NO. 22), 3A5-80R 5'-CAG GGA GTT GAC CTT CAT ACG TTC CC-3' (SEQ ID NO: 23) and 3A7-18R 5'-GCA TAG GCT GTT GAC AGT CAT AAA TA-3' (SEQ ID NO. 24). The amplicons were subcloned and sequenced according to standard procedures. Primer pairs to investigate the expression of ps genes were 1. for ps2: 3APs2-6F (5'-AAC AGC ACA CAG CTG AAA GT 3' (SEQ ID NO: 25)) and 3APs2-7R (5' CTG ATG GTA GGA CAA AGT AG-3' (SEQ ID NO. 26)), 3APs2-5F (5'-CCT GGT GCT CCT CTA TCT ATA TGG AG-3' (SEQ ID NO. 27)) and 3A5-18R ( 5'-GGG AGT TGA CCT TCA TAC GTT C-3' (SEQ ID NO. 28)); 2. for ps3: 3APs3-1F (5'-CAA ACT TTG CCA TGG AAA TG-3' (SEQ ID NO: 29)) and 3AX-60R (5'-TTG AGG CGA CTT TCT TTC ATC CTT TCA ATG-3' (SEQ ID NO: 30)); 3. for ps1: 3APs1-3F (5'-AAA TCT TGG CAT TCC AGG T-3' (SEQ ID NO: 31)) and 3A7-16R (5'-TAG GCT GTT GAC AGT CAT AAA TA-3' (SEQ ID NO. 32)).

Example 4

POLYMORPHISM SEARCH

Oligonucleotides were selected from intron sequence surrounding CYP3AX exons and their gene specificity was tested on a panel of 8 DNA samples obtained from different Caucasian individuals. The exon 9 polymorphism reported here was detected here using oligonucleotides 3AX-38F 5'-GCT CTC CAA GGT TTT AGA TGC-3' (SEQ ID NO. 33) and 3AX-41R 5'- GGG AGT GCC ACA CTT GTT C-3' (SEQ ID NO: 34). The PCR conditions were: 94° C., 2 min (1×), 94° C., 45 sec, 62° C., 45 sec, 72° C., 1 min (34×) and 72° C., 10 min (1×).

Example 5

INDUCTION OF CYP3A IN PRIMARY HUMAN HEPATOCYTES

Primary human hepatocytes were isolated from normal hepatic tissue surrounding a liver tumor. One million cells were plated per well of a collagen-coated 6-well plate. After 24 h of culture in 5% FCS, the cells were serum-starved for 48 h. Subsequently, they were cultured for 48 h in the same serum-free medium in the presence of 10 uM of Rifampicin (Sigma), dissolved in DMSO (final concentration of DMSO in cell culture medium was 0.1%). Following lysis with 0.5% NP-40 in the RLN buffer (50 mM TRIS-HCL, pH 8.0, 140 mM NaCl, 1.5 mM MgCl$_2$, 1 mM DTT, 1000 U/ml RNAsin), the lysates were briefly centrifuged to collect cell nuclei and the supernatant was used for RNA isolation.

Example 6

THE SEQUENCE OF THE CYP3A LOCUS

The CYP3A locus has been assigned to 7q21.1 (Inoue, Jpn. J Hum. Genet. 37 (1992), 133–8; Jounaidi, Biochem. Biophys. Res. Commun. 205 (1994), 1741"7). A bacterial artificial chromosome (BAC) had been isolated by Genome Systems (BAC No. 22300) from a human genomic BAC library using oligonucleotides derived from the promoter region of CYP3A4 (Rebbeck, J. Natl. Cancer Inst. 90 (1998), 1225–9). Nine hundred and sixty clones were picked for DNA isolation and sequencing. This was followed by three rounds of gap closing which involved direct sequencing of the BAC DNA as well as sequence editing. The length of the BAC 22300 genomic insert has been determined as 174832 bp.

In the following, the sequence was extended on both ends by overlapping, non-annotated contigs from BACs with accession numbers AC011904 and AC005020, which had been retrieved from the NCBI's HTGS databank using a BLAST search. FIG. 1 shows schematically the resulting CYP3A locus sequence which is 231456 bp long (orientation arbitrary). The sequence of the BAC 22300 corresponds to bp 32011 to 206842 and its expected error rate is estimated as 0.01 per 10 kb (1 error in 1000 kb), which is equal to an average Phred score of 60. Consistently, no significant differences between the BAC 22300 sequence and CYP3A cDNA, or genomic (FIG. 1), sequences deposited in GenBank has been detected. The only major difference is a 111 bp insertion at position 104280 of the CYP3A locus which was found in a CYP3A4 genomic sequence with the GenBank accession number AF209389. The insertion is localized in intron 3 of CYP3A4 and its preliminary analysis using several Caucasian genomic DNA samples suggests that it may represent an allelic variant specific for Chinese population. The sequences with GenBank accession numbers AC011904 and AC005020, which form the flanking parts of the CYP3A locus, represent working draft ("unfinished") sequences and could contain more errors than the sequence of the BAC 22300. However, no differences between AC011904 and AC005020 sequences and the corresponding CYP3A cDNA sequences have been detected.

Example 7

GENOMIC ORGANIZATION OF THE CYP3A LOCUS

The genomic organization of the CYP3A locus was analyzed for the presence and organization of genes. Genomic repeats, which account for 21% of the sequence (not shown) were masked and the resulting sequence was subjected to an expressed site tag (EST) mapping using the EMBL's EST Databank (Release 58). The analysis revealed the presence of the three known CYP3A genes (CYP3A4, CYP3A5 and CYP3A7) (FIG. 1). In addition to the known CYP3A genes, the locus contains several regions with strong homology to CYP3A cDNA, which are depicted in FIG. 1 as ps1__1, ps1__2, ps2__1, ps2__2, and ps3__1. These regions correspond either to exon 1 or 2 of CYP3A genes and their positions within the locus sequence are given in Table 2. Surprisingly, also a fourth CYP3A gene named CYP3AX (FIG. 1) was detected. The localization of exons of the four CYP3A genes within the locus is given in Table 1. The 5' ends of exon 1 given in Table 1 correspond to the respective first bases of CYP3A4, CYP3A5, CYP3A7 and CYP3AX transcripts, as determined by Rapid Amplification of cDNA ends (RACE) (FIG. 2). The numbering of the 3' ends of exon 13 is based on the GenBank cDNA sequences with accession numbers M14096 (CYP3A4), NM__000777.1 (CYP3A5) and NM__000765.1 (CYP3A7) and on the CYP3AX cDNA sequence shown in FIG. 3. Exon 1 through 13 genomic distances are 26.5 kb (CYP3A4), 31.8 kb (CYP3A5), 30.2 kb CYP3A7 and 37 kb (CYP3AX).

The localization and orientation of the mentioned regions as well as the presence of open reading frames and of the consensus splice sites suggested their possible utilization in the formation of alternative 5' ends of CYP3A7, CYP3A5 and CYP3AX transcripts, respectively. The elucidation of a function of the ps2 homology regions was especially important since the 5' genomic region adjacent to ps2_1 had been previously identified as a CYP3A5 promoter (Jounaidi, Biochem. Biophys. Res. Commun. 205 (1994), 1741-7). The expression of the putative ps transcripts by PCR amplification of cDNA pools derived from 8 liver samples using various combinations of primer pairs derived from ps1 and CYP3A7, ps2 and CYP3A5, and ps3_1 and CYP3AX, respectively, has been investigated. The experiments haven't provided any evidence for the utilization of ps regions as alternative 5' ends of CYP3A genes (data not shown). In addition, no ps2 sequence has been found in the 5'-RACE experiments to determine the transcriptional start site of CYP3A5 (see above). All this suggests that ps regions are incomplete pseudogenes of CYP3A.

The assignment as pseudogenes is based on the failure to detect the expression of exon sequences of these genes. Also, the localization of these pseudogenes in comparison with the duplication boundaries argues against their functionality. Rather, they appear to be duplication artifacts. The analysis also sheds new light on the identity and genomic localization of the CYP3A5 promoter. The sequence originally described as CYP3A5 promoter (Jounaidi, Biochem. Biophys. Res. Commun. 205 (1994), 1741-7) is in fact localized in the 5' genomic region adjacent to ps2_1. The apparently erroneous assignment of the sequence as CYP3A5 promoter was facilitated by the identity of the ps2_1 and CYP3A5 exon 1 sequences (Table 2). The 5' locus region adjacent to the CYP3A5 gene contains another, highly conserved sequence, which could serve as a promoter for the gene.

The organization of the locus suggested that it arose through several duplication events. The duplication boundaries were identified by multiple sequence alignments and their localization within the locus is shown in FIG. 1. Their positions are 85140 (CYP3AX-CYP3A4), 134110 (CYP3A4-CYP3A7) and 189480 (CYP3A7CYP3A5).

Example 8

IDENTIFICATION OF THE TRANSCRIPTIONAL START SITE OF CYP3AX

The experimental identification of the transcriptional start site and of the presumed structure of the CYP3AX transcript was performed by means of RT-PCR and 5'RACE followed by sequence analysis. The analyses were conducted on liver RNA samples based on the initial observation of the gene's expression in this organ (see below). The length of the 5' untranslated portion of the transcript determined by RACE (103 bp) is almost identical to, and its sequence highly conserved with, that of the other CYP3A genes (FIG. 2). The transcript begins with a 5' cap consensus dinucleotide GA. The 3' end of the transcript remains to be determined.

Example 9

EXPRESSION OF CYP3AX IN HUMAN TISSUES

Figure 5:
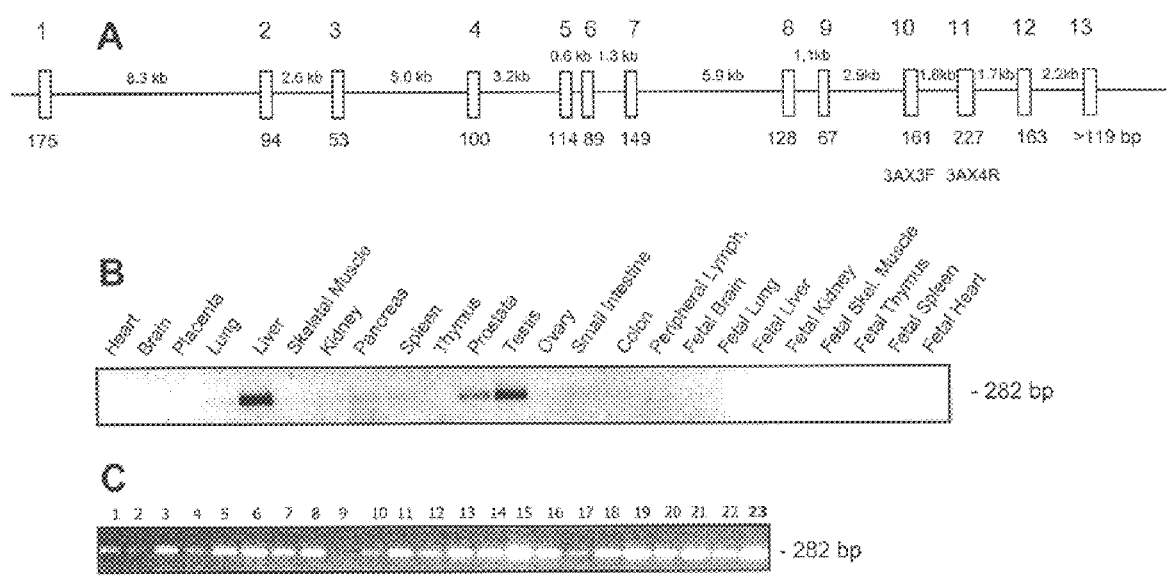
FIG. 5 shows gene structure and expression of CYP3AX (FIG. 5A). Arrowheads indicate the localization of primers used to investigate CYP3AX expression (FIG. 5B) in a panel of cDNA pools derived from 24 human tissues, and (FIG. 5C) in a panel of cDNA pools isolated from 23 human liver samples.

The expression of CYP3AX was investigated by PCR on CDNA pools derived from 24 human tissues. The oligonucleotides used are located in exons 10 and 11 of the gene (FIG. 5A). The experiment revealed the expression of the gene in the liver, in the testis and in the prostate (FIG. 5B). Weaker amplicons were obtained with cDNA pools derived from the pancreas, spleen, small intestine and colon. Furthermore, we investigated the CYP3AX expression in a panel of cDNAs derived from liver samples of 23 unrelated Caucasian individuals. As shown in FIG. 5C, CYP3AX was found to be expressed in all but one liver. The identity of the CYP3AX PCR amplicons shown in FIG. 5B–C was confirmed by sequencing (data not shown).

The expression of CYP3AX is consistent with the existence of two CYP3AX EST clones in the GenBank. A search for new members of the human CYP3A gene family revealed four expressed sequence tags (ESTs) nearly identical to the 3' part of the putative CYP3AX mRNA. The ESTs AA416822 and AA417369 are derived from a human testis cDNA clone (IMAGE clone number 731237). The ESTs H90703 and H89858 are derived from a human fetal liver/spleen library (IMAGE clone number 241686). A resequencing of the clones confirmed their identity as CYP3AX transcripts (not shown).

Example 10

EXPRESSION OF CYP3AX IN HUMAN PRIMARY

HEPATOCYTES UNDERGOES INDUCTION BY RIFAMPICIN

Figure 6:
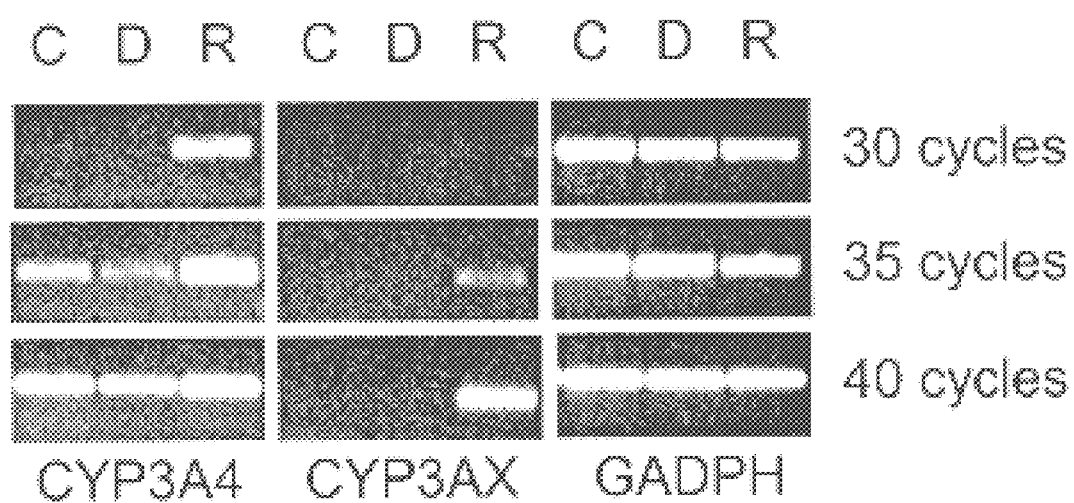
FIG. 6 shows the effect of 10 $\mu$M rifampicin on the expression of CYP3A4, CYP3AX and GADPH in primary human hepatocytes.
Figure 7:
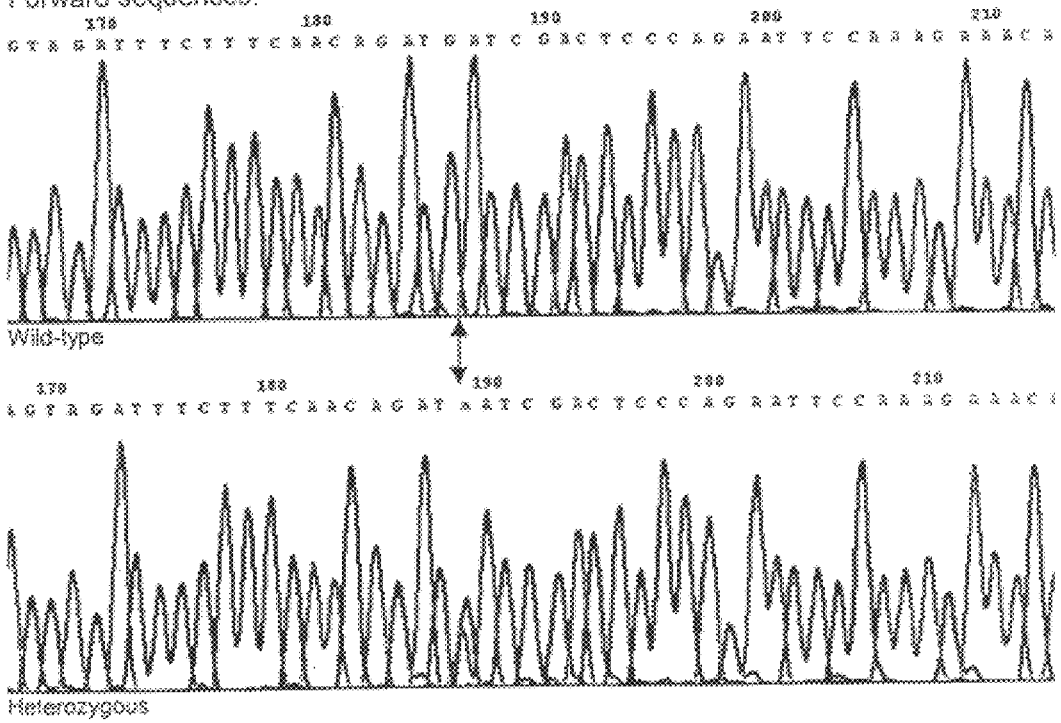
FIG. 7 shows the CPY3AX Met275Ile protein polymorphism found in one of 8 Caucasian DNA samples screened.

To investigate the inducibility of CYP3AX expression, primary human hepatocytes were treated with 10 $\mu$M rifampicin for 48 h. Afterwards, the cells were lysed, total cytoplasmic RNA isolated and 0.5 ug used for reverse transcription. The resulting hepatic cDNA pools were then investigated using primers derived from CYP3AX, CYP3A4 and from the house-keeping gene GADPH. Aliquots of the PCR reactions were removed after 20, 25, 30, 35 and 40 cycles and they were analyzed on an agarose gel. As expected, CYP3A4 expression underwent induction by rifampicin, whereas that of GADPH did not (FIG. 6). A CYP3AX transcript band was first detected after 35, and a strong band after 40, cycles and it was present only in the rifampicin-treated samples. These results indicate that CYP3AX undergoes induction by rifampicin and thus point to similarities in regulatory mechanisms between CYP3AX and CYP3A4.

EXAMPLE 11

SEARCH FOR POLYMORPHISM

To search for polymorphism, genomic DNA from randomly selected, healthy individuals was amplified with CYP3AX specific primer pairs and the amplified fragments were completely sequenced in both directions.

Diagnostic tests can be developed to easily detect mutations in genomic DNA. Each Mutation could be shown to either abolish or create an enzymatic restriction site. It may be thus possible to develop an assay based on 1) CYP3AX-specific amplification of the gene fragment that contains the mutation and 2) digestion with a suitable restriction enzyme. The frequency of each mutation may be estimated in a representative population using the diagnostic test designed for it.

TABLE 1

|  | CYP3AX (−) | | CYP3A4 (+) | | CYP3A7 (−) | | CYP3A5 (+) | |
| --- | --- | --- | --- | --- | --- | --- | --- | --- |
|  | Begin | End | Begin | End | Begin | End | Begin | End |
| Exon 1 | 50101 | 49928 | 93944 | 94117 | 142916 | 143089 | 198128 | 198300 |
| Exon 2 | 41661 | 41568 | 98044 | 98137 | 146960 | 147053 | 201918 | 202011 |
| Exon 3 | 38994 | 38942 | 100049 | 100101 | 155765 | 155817 | 203546 | 203598 |
| Exon 4 | 33971 | 33872 | 105430 | 105529 | 157701 | 157800 | 205452 | 205551 |
| Exon 5 | 30626 | 30513 | 107884 | 107997 | 160475 | 160588 | 211066 | 211179 |
| Exon 6 | 29948 | 29860 | 108263 | 108351 | 160849 | 160937 | 211442 | 211530 |
| Exon 7 | 28568 | 28420 | 109617 | 109765 | 162208 | 162356 | 212817 | 212965 |
| Exon 8 | 22523 | 22396 | 110861 | 110988 | 163432 | 163559 | 214036 | 214163 |
| Exon 9 | 21281 | 21215 | 111676 | 111742 | 164579 | 164645 | 215249 | 215315 |
| Exon 10 | 18284 | 18124 | 114104 | 114264 | 167225 | 167385 | 217472 | 217632 |
| Exon 11 | 16501 | 16275 | 115852 | 116078 | 168860 | 169086 | 225352 | 225578 |
| Exon 12 | 14577 | 14415 | 117138 | 117300 | 170147 | 170309 | 227899 | 228058 |
| Exon 13 | 12208 | 12090 | 119891 | 120442 | 172526 | 173077 | 229731 | 229937 |

Exon boundaries of the four CYP3A genes. Exon mapping based on the results of 5'-RACE and CYP3A cDNA sequences with GenBank accession numbers M14096 (CYP3A4), NM_000777.1 (CYP3A5) and NM_000765.1 as well as on CYP3AX cDNA sequence shown in FIG. 3.

TABLE 2

| Exon | Strand | Position | | homology | |
| --- | --- | --- | --- | --- | --- |
|  |  | begin | End | in % | to |
| ps3_1 | minus | 58197 | 58026 | 85.5 | cyp3ax exon1 |
| ps1_1 | plus | 125525 | 125698 | 83.9 | cyp3a7 exon1 |
| ps1_2 | plus | 129777 | 129870 | 79.8 | cyp3a7 exon2 |
| ps2_1 | plus | 177983 | 178156 | 100.0 | cyp3a5 exon1 |
| ps2_2 | plus | 182287 | 182380 | 80.9 | cyp3a5 exon2 |

Exon boundaries of the CYP3A pseudogenes within the CYP3A locus and their homology to the respective regions of the immediate downstream CYP3A homologue.

TABLE 3

|  | Cyp3a4.pro | cyp3a5.pro | cyp3a7.pro | cyp3ax.pro |  |
| --- | --- | --- | --- | --- | --- |
| cyp3a4.pro | *** | 84.1 | 88.1 | 75.8 | cyp3a4.pro |
| cyp3a5.pro | 17.9 | *** | 81.9 | 75.8 | cyp3a5.pro |

TABLE 3-continued

|  | Cyp3a4.pro | cyp3a5.pro | cyp3a7.pro | cyp3ax.pro |  |
| --- | --- | --- | --- | --- | --- |
| cyp3a7.pro | 13.0 | 20.7 | *** | 71.5 | cyp3a7.pro |
| cyp3ax.pro | 29.2 | 29.3 | 35.9 | *** | cyp3ax.pro |
|  | cyp3a4.pro | cyp3a5.pro | cyp3a7.pro | cyp3ax.pro |  |

Identity and divergence among the CYP3A proteins. Percent identity in upper triangle, percent divergence in lower triangle. Calculation based on GenBank accession numbers M14096 (CYP3A4), NM_000777.1 (CYP3A5) and NTM_000765.1 (CYP3A7) and the CYP3AX protein sequence shown in FIG. 3.

It will be clear that the invention may be practiced otherwise than as particularly described in the foregoing description and examples. Numerous modifications and variations of the present invention are possible in light of the above teachings and, therefore, arc within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated by reference. Moreover, the sequence listing is herein incorporated by reference.

What is claimed is:

1. An isolated polynucleotide encoding a cytochrome P450 (CYP) 3AX polypeptide that retains biological activity, selected from the group consisting of:
   (a) a polynucleotide encoding a polypeptide comprising the amino acid sequence depicted in SEQ ID NO: 2, 4, 6, 8, 10 or 12;
   (b) a polynucleotide encoding a polypeptide, said polynucleotide comprising a coding sequence as depicted in any one of SEQ ID NO: 1, 3, 5, 7, 9 or 11; and
   (c) a polynucleotide the nucleotide sequence of which is a variant of the nucleotide sequence of a polynucleotide of any one of (a) to (b), due to genetic code degeneracy;
   provided that the polynucleotide does not consist of the nucleotide sequence set forth in SEQ ID NO: 35, in SEQ ID NO: 36, in SEQ ID NO: 37 or in SEQ ID NO: 38.

2. The polynucleotide of claim 1 which is DNA.

3. The polynucleotide of claim 2 which is genomic DNA.

4. The polynucleotide of claim 1 which is RNA.

5. The polynucleotide of any one of claims 1 to 4, wherein the polynucleotide is operatively linked to an expression control sequence.

6. A vector comprising the polynucleotide of claim 1.

7. A vector comprising the polynucleotide of claim 1 operatively linked to an expression control sequence.

8. A host cell comprising the polynucleotide of claim 1.

9. A host cell comprising the polynucleotide of claim 1 operatively linked to an expression control sequence.

10. A host cell comprising a vector wherein the vector comprises the polynucleotide of claim 1 operatively linked to an expression control sequence.

11. A method for producing a CYP3AX polypeptide or fragment thereof comprising:
   (a) culturing a host cell selected from the group consisting of the host cell of claim 9 and the host cell of claim 10, under conditions and a time sufficient to permit expression of a CYP3AX polypeptide or fragment thereof; and (b) isolating said CYP3AX polypeptide or fragment thereof from the host cell culture.

12. A method for producing a cell capable of expressing a CYP3AX polypeptide comprising genetically engineering a cell with a polynucleotide according to claim 1.

13. A method for producing a cell capable of expressing a CYP3AX polypeptide comprising genetically engineering a cell with a polynucleotide according to claim 1 that is operatively linked to an expression control sequence.

14. A method for producing a cell capable of expressing a CYP3AX polypeptide comprising genetically engineering a cell with a vector comprising the polynucleotide of claim 1.

15. A method for producing a cell capable of expressing a CYP3AX polypeptide comprising genetically engineering a cell with a vector comprising the polynucleotide of claim 1 that is operatively linked to an expression control sequence.

16. An isolated gene encoding a CYP3AX protein or polypeptide fragment thereof that is encoded by the polynucleotide of claim 1.

17. An isolated nucleic acid molecule comprising a nucleic acid sequence that is complementary to the polynucleotide of claim 1.

18. A vector comprising the nucleic acid molecule of claim 17.

19. A nucleic acid molecule that is capable of specifically recognizing and cleaving the polynucleotide of claim 1.

20. A vector comprising the nucleic acid molecule of claim 19.

21. A CYP3AX-specific primer or probe consisting of an oligonucleotide that is about 15 to 50 nucleotides in length and that comprises a nucleotide sequence selected from the group consisting of a portion of SEQ ID NO: 1 and a complementary sequence thereto.

22. A composition comprising at least one member selected from the group consisting of (a) the polynucleotide of any one of claims 1 to 2, (b) the vector of claim 6 or claim 7, (c) the host cell of any one of claims 8–10 or a cell produced according to the method of any one of claims 12–15, (d) the nucleic acid molecule of either claim 19 or 19, (e) the vector of either claim 18 or 20, and (f) the primer or probe of claim 21.

* * * * *

SEQUENCE LISTING

```
<160> NUMBER OF SEQ ID NOS: 45

<210> SEQ ID NO 1
<211> LENGTH: 1659
<212> TYPE: DNA
<213> ORGANISM: Homo sapiens
<220> FEATURE:
<221> NAME/KEY: CDS
<222> LOCATION: (105)..(1616)

<400> SEQUENCE: 1
gacctctggg cagagaaaca aagctctata tgcacagccc agcaaagagc agcacacagc      60
tgaaagaaaa actcagaaga cagagctgaa aaagaaaact ggtg atg gat ctc att     116
                                              Met Asp Leu Ile
                                                1
```

| | |
|---|---|
| cca aac ttt gcc atg gaa aca tgg gtt ctt gtg gct acc agc ctg gta<br>Pro Asn Phe Ala Met Glu Thr Trp Val Leu Val Ala Thr Ser Leu Val<br>5                  10                15                20 | 164 |
| ctc ctc tat att tat ggg acc cat tca cat aaa ctt ttt aag aag ctg<br>Leu Leu Tyr Ile Tyr Gly Thr His Ser His Lys Leu Phe Lys Lys Leu<br>                25                30                35 | 212 |
| gga att cct ggg cca acc cct ctg cct ttt ctg gga act att ttg ttc<br>Gly Ile Pro Gly Pro Thr Pro Leu Pro Phe Leu Gly Thr Ile Leu Phe<br>            40                45                50 | 260 |
| tac ctt agg ggt ctt tgg aat ttt gac aga gaa tgt aat gaa aaa tac<br>Tyr Leu Arg Gly Leu Trp Asn Phe Asp Arg Glu Cys Asn Glu Lys Tyr<br>        55                60                65 | 308 |
| gga gaa atg tgg ggg ctg tat gag ggg caa cag ccc atg ctg gtc atc<br>Gly Glu Met Trp Gly Leu Tyr Glu Gly Gln Gln Pro Met Leu Val Ile<br>70                  75                80 | 356 |
| atg gat ccc gac atg atc aaa aca gtg tta gtg aaa gaa tgt tac tct<br>Met Asp Pro Asp Met Ile Lys Thr Val Leu Val Lys Glu Cys Tyr Ser<br>85                  90                95              100 | 404 |
| gtc ttc aca aac cag atg cct tta ggt cca atg gga ttt ctg aaa agt<br>Val Phe Thr Asn Gln Met Pro Leu Gly Pro Met Gly Phe Leu Lys Ser<br>                105              110             115 | 452 |
| gcc tta agt ttt gct gaa gat gaa gaa tgg aag aga ata cga aca ttg<br>Ala Leu Ser Phe Ala Glu Asp Glu Glu Trp Lys Arg Ile Arg Thr Leu<br>            120                125             130 | 500 |
| cta tct cca gct ttc acc agt gta aaa ttc aag gaa atg gtc ccc atc<br>Leu Ser Pro Ala Phe Thr Ser Val Lys Phe Lys Glu Met Val Pro Ile<br>            135              140             145 | 548 |
| att tcc caa tgt gga gat atg ttg gtg aga agc ctg agg cag gaa gca<br>Ile Ser Gln Cys Gly Asp Met Leu Val Arg Ser Leu Arg Gln Glu Ala<br>150                 155               160 | 596 |
| gag aac agc aag tcc atc aac ttg aaa gat ttc ttt ggg gcc tac acc<br>Glu Asn Ser Lys Ser Ile Asn Leu Lys Asp Phe Phe Gly Ala Tyr Thr<br>165                 170               175             180 | 644 |
| atg gat gta atc act ggc aca tta ttt gga gtg aac ttg gat tct ctc<br>Met Asp Val Ile Thr Gly Thr Leu Phe Gly Val Asn Leu Asp Ser Leu<br>                185              190             195 | 692 |
| aac aat cca caa gat ccc ttt ctg aaa aat atg aag aag ctt tta aaa<br>Asn Asn Pro Gln Asp Pro Phe Leu Lys Asn Met Lys Lys Leu Leu Lys<br>            200                205             210 | 740 |
| ttg gat ttt ttg gat ccc ttt tta ctc tta ata tca ctc ttt cca ttt<br>Leu Asp Phe Leu Asp Pro Phe Leu Leu Leu Ile Ser Leu Phe Pro Phe<br>            215              220             225 | 788 |
| ctt acc cca gtt ttt gaa gcc cta aat atc ggt ttg ttt cca aaa gat<br>Leu Thr Pro Val Phe Glu Ala Leu Asn Ile Gly Leu Phe Pro Lys Asp<br>230                 235               240 | 836 |
| gtt acc cat ttt tta aaa aat tcc att gaa agg atg aaa gaa agt cgc<br>Val Thr His Phe Leu Lys Asn Ser Ile Glu Arg Met Lys Glu Ser Arg<br>245                 250               255             260 | 884 |
| ctc aaa gat aaa caa aag cat cga gta gat ttc ttt caa cag atg atc<br>Leu Lys Asp Lys Gln Lys His Arg Val Asp Phe Phe Gln Gln Met Ile<br>            265              270             275 | 932 |
| gac tcc cag aat tcc aaa gaa aca aag tcc cat aaa gct ctg tct gat<br>Asp Ser Gln Asn Ser Lys Glu Thr Lys Ser His Lys Ala Leu Ser Asp<br>            280              285             290 | 980 |
| ctg gag ctt gtg gcc cag tca att atc atc att ttt gct gcc tat gac<br>Leu Glu Leu Val Ala Gln Ser Ile Ile Ile Ile Phe Ala Ala Tyr Asp<br>            295              300             305 | 1028 |
| aca act agc acc act ctc ccc ttc att atg tat gaa ctg gcc act cac<br>Thr Thr Ser Thr Thr Leu Pro Phe Ile Met Tyr Glu Leu Ala Thr His | 1076 |

-continued

```
            310                 315                 320
cct gat gtc cag cag aaa ctg cag gag gag att gac gca gtt tta ccc      1124
Pro Asp Val Gln Gln Lys Leu Gln Glu Glu Ile Asp Ala Val Leu Pro
325                 330                 335                 340 aat aag gca cct gtc acc tac gat gcc ctg gta cag atg gag tac ctt      1172
Asn Lys Ala Pro Val Thr Tyr Asp Ala Leu Val Gln Met Glu Tyr Leu
                345                 350                 355 gac atg gtg gtg aat gaa acg ctc aga tta ttc cca gtt gtt agt aga      1220
Asp Met Val Val Asn Glu Thr Leu Arg Leu Phe Pro Val Val Ser Arg
            360                 365                 370 gtt acg aga gtc tgc aag aaa gat att gaa atc aat gga gtg ttc att      1268
Val Thr Arg Val Cys Lys Lys Asp Ile Glu Ile Asn Gly Val Phe Ile
        375                 380                 385 ccc aaa ggg tta gca gtg atg gtt cca atc tat gct ctt cac cat gac      1316
Pro Lys Gly Leu Ala Val Met Val Pro Ile Tyr Ala Leu His His Asp
390                 395                 400 cca aag tac tgg aca gag cct gag aag ttc tgc cct gaa agg ttc agt      1364
Pro Lys Tyr Trp Thr Glu Pro Glu Lys Phe Cys Pro Glu Arg Phe Ser
405                 410                 415                 420 aag aag aac aag gac agc ata gat ctt tac aga tac ata cct ttt gga      1412
Lys Lys Asn Lys Asp Ser Ile Asp Leu Tyr Arg Tyr Ile Pro Phe Gly
                425                 430                 435 gct gga ccc cga aac tgc att ggc atg agg ttt gct ctc aca aac ata      1460
Ala Gly Pro Arg Asn Cys Ile Gly Met Arg Phe Ala Leu Thr Asn Ile
            440                 445                 450 aaa ctt gct gtc att aga gca ctg cag aac ttc tcc ttc aaa cct tgt      1508
Lys Leu Ala Val Ile Arg Ala Leu Gln Asn Phe Ser Phe Lys Pro Cys
        455                 460                 465 aaa gag act cag atc cca ctg aaa tta gac aat cta cca att ctt caa      1556
Lys Glu Thr Gln Ile Pro Leu Lys Leu Asp Asn Leu Pro Ile Leu Gln
470                 475                 480 cca gaa aaa cct att gtt cta aaa gtg cac tta aga gat ggg att aca      1604
Pro Glu Lys Pro Ile Val Leu Lys Val His Leu Arg Asp Gly Ile Thr
485                 490                 495                 500 agt gga ccc tga ctttccctaa ggacttccac tttgttcaag aaagctgtat ccc      1659
Ser Gly Pro
```

<210> SEQ ID NO 2
<211> LENGTH: 503
<212> TYPE: PRT
<213> ORGANISM: Homo sapiens

<400> SEQUENCE: 2

```
Met Asp Leu Ile Pro Asn Phe Ala Met Glu Thr Trp Val Leu Val Ala
 1               5                  10                  15

Thr Ser Leu Val Leu Leu Tyr Ile Tyr Gly Thr His Ser His Lys Leu
                20                  25                  30

Phe Lys Lys Leu Gly Ile Pro Gly Pro Thr Pro Leu Pro Phe Leu Gly
            35                  40                  45

Thr Ile Leu Phe Tyr Leu Arg Gly Leu Trp Asn Phe Asp Arg Glu Cys
        50                  55                  60

Asn Glu Lys Tyr Gly Glu Met Trp Gly Leu Tyr Glu Gly Gln Gln Pro
65                  70                  75                  80

Met Leu Val Ile Met Asp Pro Asp Met Ile Lys Thr Val Leu Val Lys
                85                  90                  95

Glu Cys Tyr Ser Val Phe Thr Asn Gln Met Pro Leu Gly Pro Met Gly
                100                 105                 110

Phe Leu Lys Ser Ala Leu Ser Phe Ala Glu Asp Glu Glu Trp Lys Arg
```

```
                115                 120                 125
Ile Arg Thr Leu Leu Ser Pro Ala Phe Thr Ser Val Lys Phe Lys Glu
    130                 135                 140

Met Val Pro Ile Ile Ser Gln Cys Gly Asp Met Leu Val Arg Ser Leu
145                 150                 155                 160

Arg Gln Glu Ala Glu Asn Ser Lys Ser Ile Asn Leu Lys Asp Phe Phe
                165                 170                 175

Gly Ala Tyr Thr Met Asp Val Ile Thr Gly Thr Leu Phe Gly Val Asn
            180                 185                 190

Leu Asp Ser Leu Asn Asn Pro Gln Asp Pro Phe Leu Lys Asn Met Lys
        195                 200                 205

Lys Leu Leu Lys Leu Asp Phe Leu Asp Pro Phe Leu Leu Ile Ser
    210                 215                 220

Leu Phe Pro Phe Leu Thr Pro Val Phe Glu Ala Leu Asn Ile Gly Leu
225                 230                 235                 240

Phe Pro Lys Asp Val Thr His Phe Leu Lys Asn Ser Ile Glu Arg Met
                245                 250                 255

Lys Glu Ser Arg Leu Lys Asp Lys Gln Lys His Arg Val Asp Phe Phe
            260                 265                 270

Gln Gln Met Ile Asp Ser Gln Asn Ser Lys Glu Thr Lys Ser His Lys
        275                 280                 285

Ala Leu Ser Asp Leu Glu Leu Val Ala Gln Ser Ile Ile Ile Phe
    290                 295                 300

Ala Ala Tyr Asp Thr Thr Ser Thr Thr Leu Pro Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Val Thr Tyr Asp Ala Leu Val Gln
            340                 345                 350

Met Glu Tyr Leu Asp Met Val Val Asn Glu Thr Leu Arg Leu Phe Pro
        355                 360                 365

Val Val Ser Arg Val Thr Arg Val Cys Lys Lys Asp Ile Glu Ile Asn
    370                 375                 380

Gly Val Phe Ile Pro Lys Gly Leu Ala Val Met Val Pro Ile Tyr Ala
385                 390                 395                 400

Leu His His Asp Pro Lys Tyr Trp Thr Glu Pro Glu Lys Phe Cys Pro
                405                 410                 415

Glu Arg Phe Ser Lys Lys Asn Lys Asp Ser Ile Asp Leu Tyr Arg Tyr
            420                 425                 430

Ile Pro Phe Gly Ala Gly Pro Arg Asn Cys Ile Gly Met Arg Phe Ala
        435                 440                 445

Leu Thr Asn Ile Lys Leu Ala Val Ile Arg Ala Leu Gln Asn Phe Ser
    450                 455                 460

Phe Lys Pro Cys Lys Glu Thr Gln Ile Pro Leu Lys Leu Asp Asn Leu
465                 470                 475                 480

Pro Ile Leu Gln Pro Glu Lys Pro Ile Val Leu Lys Val His Leu Arg
                485                 490                 495

Asp Gly Ile Thr Ser Gly Pro
            500

<210> SEQ ID NO 3
<211> LENGTH: 1515
<212> TYPE: DNA
<213> ORGANISM: Homo sapiens
```

-continued

```
<220> FEATURE:
<221> NAME/KEY: CDS
<222> LOCATION: (1)..(1515)

<400> SEQUENCE: 3 atg gat ctc att cca aac ttt gcc atg gaa aca tgg gtt ctt gtg gct      48
Met Asp Leu Ile Pro Asn Phe Ala Met Glu Thr Trp Val Leu Val Ala
 1               5                  10                  15 acc agc ctg gta ctc ctc tat att tat ggg acc cat tca cat aaa ctt      96
Thr Ser Leu Val Leu Leu Tyr Ile Tyr Gly Thr His Ser His Lys Leu
             20                  25                  30 ttt aag aag ctg gga att cct ggg cca acc cct ctg cct ttt ctg gga     144
Phe Lys Lys Leu Gly Ile Pro Gly Pro Thr Pro Leu Pro Phe Leu Gly
         35                  40                  45 act att ttg ttc tac ctt agg ggt ctt tgg aat ttt gac aga gaa tgt     192
Thr Ile Leu Phe Tyr Leu Arg Gly Leu Trp Asn Phe Asp Arg Glu Cys
     50                  55                  60 aat gaa aaa tac gga gaa atg tgg ggg ctg tat gag ggg caa cag ccc     240
Asn Glu Lys Tyr Gly Glu Met Trp Gly Leu Tyr Glu Gly Gln Gln Pro
 65                  70                  75                  80 atg ctg gtc atc atg gat ccc gac atg atc aaa aca gtg tta gtg aaa     288
Met Leu Val Ile Met Asp Pro Asp Met Ile Lys Thr Val Leu Val Lys
                 85                  90                  95 gaa tgt tac tct gtc ttc aca aac cag atg cct tta ggt cca atg gga     336
Glu Cys Tyr Ser Val Phe Thr Asn Gln Met Pro Leu Gly Pro Met Gly
            100                 105                 110 ttt ctg aaa agt gcc tta agt ttt gct gaa gat gaa gaa tgg aag aga     384
Phe Leu Lys Ser Ala Leu Ser Phe Ala Glu Asp Glu Glu Trp Lys Arg
        115                 120                 125 ata cga aca ttg cta tct cca gct ttc acc agt gta aaa ttc aag gaa     432
Ile Arg Thr Leu Leu Ser Pro Ala Phe Thr Ser Val Lys Phe Lys Glu
    130                 135                 140 atg gtc ccc atc att tcc caa tgt gga gat atg ttg gtg aga agc ctg     480
Met Val Pro Ile Ile Ser Gln Cys Gly Asp Met Leu Val Arg Ser Leu
145                 150                 155                 160 agg cag gaa gca gag aac agc aag tcc atc aac ttg aaa gat ttc ttt     528
Arg Gln Glu Ala Glu Asn Ser Lys Ser Ile Asn Leu Lys Asp Phe Phe
                165                 170                 175 ggg gcc tac acc atg gat gta atc act ggc aca tta ttt gga gtg aac     576
Gly Ala Tyr Thr Met Asp Val Ile Thr Gly Thr Leu Phe Gly Val Asn
            180                 185                 190 ttg gat tct ctc aac aat cca caa gat ccc ttt ctg aaa aat atg aag     624
Leu Asp Ser Leu Asn Asn Pro Gln Asp Pro Phe Leu Lys Asn Met Lys
        195                 200                 205 aag ctt tta aaa ttg gat ttt ttg gat ccc ttt tta ctc tta ata tca     672
Lys Leu Leu Lys Leu Asp Phe Leu Asp Pro Phe Leu Leu Leu Ile Ser
    210                 215                 220 ctc ttt cca ttt ctt acc cca gtt ttt gaa gcc cta aat atc ggt ttg     720
Leu Phe Pro Phe Leu Thr Pro Val Phe Glu Ala Leu Asn Ile Gly Leu
225                 230                 235                 240 ttt cca aaa gat gtt acc cat ttt tta aaa aat tcc att gaa agg atg     768
Phe Pro Lys Asp Val Thr His Phe Leu Lys Asn Ser Ile Glu Arg Met
                245                 250                 255 aaa gaa agt cgc ctc aaa gat aaa caa aag cat cga gta gat ttc ttt     816
Lys Glu Ser Arg Leu Lys Asp Lys Gln Lys His Arg Val Asp Phe Phe
            260                 265                 270 caa cag atg atc gac tcc cag aat tcc aaa gaa aca aag tcc cat aaa     864
Gln Gln Met Ile Asp Ser Gln Asn Ser Lys Glu Thr Lys Ser His Lys
        275                 280                 285 gct ctg tct gat ctg gag ctt gtg gcc cag tca att atc atc att ttt     912
```

```
Ala Leu Ser Asp Leu Glu Leu Val Ala Gln Ser Ile Ile Ile Ile Phe
        290                 295                 300 gct gcc tat gac aca act agc acc act ctc ccc ttc att atg tat gaa      960
Ala Ala Tyr Asp Thr Thr Ser Thr Thr Leu Pro Phe Ile Met Tyr Glu
305                 310                 315                 320 ctg gcc act cac cct gat gtc cag cag aaa ctg cag gag gag att gac     1008
Leu Ala Thr His Pro Asp Val Gln Gln Lys Leu Gln Glu Glu Ile Asp
            325                 330                 335 gca gtt tta ccc aat aag gca cct gtc acc tac gat gcc ctg gta cag     1056
Ala Val Leu Pro Asn Lys Ala Pro Val Thr Tyr Asp Ala Leu Val Gln
        340                 345                 350 atg gag tac ctt gac atg gtg gtg aat gaa acg ctc aga tta ttc cca     1104
Met Glu Tyr Leu Asp Met Val Val Asn Glu Thr Leu Arg Leu Phe Pro
    355                 360                 365 gtt gtt agt aga gtt acg aga gtc tgc aag aaa gat att gaa atc aat     1152
Val Val Ser Arg Val Thr Arg Val Cys Lys Lys Asp Ile Glu Ile Asn
370                 375                 380 gga gtg ttc att ccc aaa ggg tta gca gtg atg gtt cca atc tat gct     1200
Gly Val Phe Ile Pro Lys Gly Leu Ala Val Met Val Pro Ile Tyr Ala
385                 390                 395                 400 ctt cac cat gac cca aag tac tgg aca gag cct gag aag ttc tgc cct     1248
Leu His His Asp Pro Lys Tyr Trp Thr Glu Pro Glu Lys Phe Cys Pro
            405                 410                 415 gaa agt agg ttc agt aag aag aac aag gac agc ata gat ctt tac aga     1296
Glu Ser Arg Phe Ser Lys Lys Asn Lys Asp Ser Ile Asp Leu Tyr Arg
        420                 425                 430 tac ata cct ttt gga gct gga ccc cga aac tgc att ggc atg agg ttt     1344
Tyr Ile Pro Phe Gly Ala Gly Pro Arg Asn Cys Ile Gly Met Arg Phe
    435                 440                 445 gct ctc aca aac ata aaa ctt gct gtc att aga gca ctg cag aac ttc     1392
Ala Leu Thr Asn Ile Lys Leu Ala Val Ile Arg Ala Leu Gln Asn Phe
450                 455                 460 tcc ttc aaa cct tgt aaa gag act cag atc cca ctg aaa tta gac aat     1440
Ser Phe Lys Pro Cys Lys Glu Thr Gln Ile Pro Leu Lys Leu Asp Asn
465                 470                 475                 480 cta cca att ctt caa cca gaa aaa cct att gtt cta aaa gtg cac tta     1488
Leu Pro Ile Leu Gln Pro Glu Lys Pro Ile Val Leu Lys Val His Leu
            485                 490                 495 aga gat ggg att aca agt gga ccc tga                                 1515
Arg Asp Gly Ile Thr Ser Gly Pro
            500

<210> SEQ ID NO 4
<211> LENGTH: 504
<212> TYPE: PRT
<213> ORGANISM: Homo sapiens

<400> SEQUENCE: 4

Met Asp Leu Ile Pro Asn Phe Ala Met Glu Thr Trp Val Leu Val Ala
1               5                   10                  15

Thr Ser Leu Val Leu Leu Tyr Ile Tyr Gly Thr His Ser His Lys Leu
            20                  25                  30

Phe Lys Lys Leu Gly Ile Pro Gly Pro Thr Pro Leu Pro Phe Leu Gly
        35                  40                  45

Thr Ile Leu Phe Tyr Arg Gly Leu Trp Asn Phe Asp Arg Glu Cys
    50                  55                  60

Asn Glu Lys Tyr Gly Glu Met Trp Gly Leu Tyr Glu Gly Gln Gln Pro
65                  70                  75                  80
```

-continued

```
Met Leu Val Ile Met Asp Pro Asp Met Ile Lys Thr Val Leu Val Lys
                85                  90                  95

Glu Cys Tyr Ser Val Phe Thr Asn Gln Met Pro Leu Gly Pro Met Gly
            100                 105                 110

Phe Leu Lys Ser Ala Leu Ser Phe Ala Glu Asp Glu Trp Lys Arg
        115                 120                 125

Ile Arg Thr Leu Leu Ser Pro Ala Phe Thr Ser Val Lys Phe Lys Glu
    130                 135                 140

Met Val Pro Ile Ile Ser Gln Cys Gly Asp Met Leu Val Arg Ser Leu
145                 150                 155                 160

Arg Gln Glu Ala Glu Asn Ser Lys Ser Ile Asn Leu Lys Asp Phe Phe
                165                 170                 175

Gly Ala Tyr Thr Met Asp Val Ile Thr Gly Thr Leu Phe Gly Val Asn
            180                 185                 190

Leu Asp Ser Leu Asn Asn Pro Gln Asp Pro Phe Leu Lys Asn Met Lys
        195                 200                 205

Lys Leu Leu Lys Leu Asp Phe Leu Asp Pro Phe Leu Leu Leu Ile Ser
    210                 215                 220

Leu Phe Pro Phe Leu Thr Pro Val Phe Glu Ala Leu Asn Ile Gly Leu
225                 230                 235                 240

Phe Pro Lys Asp Val Thr His Phe Leu Lys Asn Ser Ile Glu Arg Met
                245                 250                 255

Lys Glu Ser Arg Leu Lys Asp Lys Gln Lys His Arg Val Asp Phe Phe
            260                 265                 270

Gln Gln Met Ile Asp Ser Gln Asn Ser Lys Glu Thr Lys Ser His Lys
        275                 280                 285

Ala Leu Ser Asp Leu Glu Leu Val Ala Gln Ser Ile Ile Ile Ile Phe
    290                 295                 300

Ala Ala Tyr Asp Thr Thr Ser Thr Thr Leu Pro Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Val Thr Tyr Asp Ala Leu Val Gln
            340                 345                 350

Met Glu Tyr Leu Asp Met Val Val Asn Glu Thr Leu Arg Leu Phe Pro
        355                 360                 365

Val Val Ser Arg Val Thr Arg Val Cys Lys Lys Asp Ile Glu Ile Asn
    370                 375                 380

Gly Val Phe Ile Pro Lys Gly Leu Ala Val Met Val Pro Ile Tyr Ala
385                 390                 395                 400

Leu His His Asp Pro Lys Tyr Trp Thr Glu Pro Glu Lys Phe Cys Pro
                405                 410                 415

Glu Ser Arg Phe Ser Lys Asn Lys Asp Ser Ile Asp Leu Tyr Arg
            420                 425                 430

Tyr Ile Pro Phe Gly Ala Gly Pro Arg Asn Cys Ile Gly Met Arg Phe
        435                 440                 445

Ala Leu Thr Asn Ile Lys Leu Ala Val Ile Arg Ala Leu Gln Asn Phe
    450                 455                 460

Ser Phe Lys Pro Cys Lys Glu Thr Gln Ile Pro Leu Lys Leu Asp Asn
465                 470                 475                 480

Leu Pro Ile Leu Gln Pro Glu Lys Pro Ile Val Leu Lys Val His Leu
                485                 490                 495

Arg Asp Gly Ile Thr Ser Gly Pro
```

```
<210> SEQ ID NO 5
<211> LENGTH: 1349
<212> TYPE: DNA
<213> ORGANISM: Homo sapiens
<220> FEATURE:
<221> NAME/KEY: CDS
<222> LOCATION: (1)..(1260)

<400> SEQUENCE: 5 atg gat ctc att cca aac ttt gcc atg gaa aca tgg gtt ctt gtg gct      48
Met Asp Leu Ile Pro Asn Phe Ala Met Glu Thr Trp Val Leu Val Ala
 1               5                  10                  15 acc agc ctg gta ctc ctc tat att tat ggg acc cat tca cat aaa ctt      96
Thr Ser Leu Val Leu Leu Tyr Ile Tyr Gly Thr His Ser His Lys Leu
             20                  25                  30 ttt aag aag ctg gga att cct ggg cca acc cct ctg cct ttt ctg gga     144
Phe Lys Lys Leu Gly Ile Pro Gly Pro Thr Pro Leu Pro Phe Leu Gly
         35                  40                  45 act att ttg ttc tac ctt agg ggt ctt tgg aat ttt gac aga gaa tgt     192
Thr Ile Leu Phe Tyr Leu Arg Gly Leu Trp Asn Phe Asp Arg Glu Cys
     50                  55                  60 aat gaa aaa tac gga gaa atg tgg ggg ctg tat gag ggg caa cag ccc     240
Asn Glu Lys Tyr Gly Glu Met Trp Gly Leu Tyr Glu Gly Gln Gln Pro
 65                  70                  75                  80 atg ctg gtc atc atg gat ccc gac atg atc aaa aca gtg tta gtg aaa     288
Met Leu Val Ile Met Asp Pro Asp Met Ile Lys Thr Val Leu Val Lys
                 85                  90                  95 gaa tgt tac tct gtc ttc aca aac cag atg cct tta ggt cca atg gga     336
Glu Cys Tyr Ser Val Phe Thr Asn Gln Met Pro Leu Gly Pro Met Gly
            100                 105                 110 ttt ctg aaa agt gcc tta agt ttt gct gaa gat gaa gaa tgg aag aga     384
Phe Leu Lys Ser Ala Leu Ser Phe Ala Glu Asp Glu Glu Trp Lys Arg
        115                 120                 125 ata cga aca ttg cta tct cca gct ttc acc agt gta aaa ttc aag gaa     432
Ile Arg Thr Leu Leu Ser Pro Ala Phe Thr Ser Val Lys Phe Lys Glu
    130                 135                 140 atg gtc ccc atc att tcc caa tgt gga gat atg ttg gtg aga agc ctg     480
Met Val Pro Ile Ile Ser Gln Cys Gly Asp Met Leu Val Arg Ser Leu
145                 150                 155                 160 agg cag gaa gca gag aac agc aag tcc atc aac ttg aaa gat ttc ttt     528
Arg Gln Glu Ala Glu Asn Ser Lys Ser Ile Asn Leu Lys Asp Phe Phe
                165                 170                 175 ggg gcc tac acc atg gat gta atc act ggc aca tta ttt gga gtg aac     576
Gly Ala Tyr Thr Met Asp Val Ile Thr Gly Thr Leu Phe Gly Val Asn
            180                 185                 190 ttg gat tct ctc aac aat cca caa gat ccc ttt ctg aag aat atg aag     624
Leu Asp Ser Leu Asn Asn Pro Gln Asp Pro Phe Leu Lys Asn Met Lys
        195                 200                 205 aag ctt tta aaa ttg gat ttt ttg gat ccc ttt cta ctc tta ata tca     672
Lys Leu Leu Lys Leu Asp Phe Leu Asp Pro Phe Leu Leu Leu Ile Ser
    210                 215                 220 ctc ttt cca ttt ctt acc cca gtt ttt gaa gcc cta aat atc ggt ttg     720
Leu Phe Pro Phe Leu Thr Pro Val Phe Glu Ala Leu Asn Ile Gly Leu
225                 230                 235                 240 ttt cca aaa gat gtt acc cat ttt tta aaa aat tcc att gaa agg atg     768
Phe Pro Lys Asp Val Thr His Phe Leu Lys Asn Ser Ile Glu Arg Met
                245                 250                 255 aaa gaa agt cgc ctc aaa gat aaa caa aag cat cga gta gat ttc ttt     816
Lys Glu Ser Arg Leu Lys Asp Lys Gln Lys His Arg Val Asp Phe Phe
```

-continued

```
              260                 265                 270
caa cag atg atc gac tcc cag aat tcc aaa gaa aca aag tcc cat aaa      864
Gln Gln Met Ile Asp Ser Gln Asn Ser Lys Glu Thr Lys Ser His Lys
        275                 280                 285 gct ctg tct gat ctg gag ctt gtg gcc cag tca att atc att ttt          912
Ala Leu Ser Asp Leu Glu Leu Val Ala Gln Ser Ile Ile Ile Phe
    290                 295                 300 gct gcc tat gac aca act agc acc act ctc ccc ttc att atg tat gaa      960
Ala Ala Tyr Asp Thr Thr Ser Thr Thr Leu Pro Phe Ile Met Tyr Glu
305                 310                 315                 320 ctg gcc act cac cct gat gtc cag cag aaa ctg cag gag gag att gac     1008
Leu Ala Thr His Pro Asp Val Gln Gln Lys Leu Gln Glu Glu Ile Asp
                325                 330                 335 gca gtt tta ccc aat aag gca cct gtc acc tac gat gcc ctg gta cag     1056
Ala Val Leu Pro Asn Lys Ala Pro Val Thr Tyr Asp Ala Leu Val Gln
        340                 345                 350 atg gag tac ctt gac atg gtg gtg aat gaa acg ctc aga tta ttc cca     1104
Met Glu Tyr Leu Asp Met Val Val Asn Glu Thr Leu Arg Leu Phe Pro
    355                 360                 365 gtt gtt agt aga gtt acg aga gtc tgc aag aaa gat att gaa atc aat     1152
Val Val Ser Arg Val Thr Arg Val Cys Lys Lys Asp Ile Glu Ile Asn
370                 375                 380 gga gtg ttc att ccc aaa ggg tta gca gtg atg gtt cca atc tat gct     1200
Gly Val Phe Ile Pro Lys Gly Leu Ala Val Met Val Pro Ile Tyr Ala
385                 390                 395                 400 ctt cac cat gac cca aag tac tgg aca gag cct gag aag ttc tgc cct     1248
Leu His His Asp Pro Lys Tyr Trp Thr Glu Pro Glu Lys Phe Cys Pro
                405                 410                 415 gaa aga tcc cac tgaaattaga caatctacca attcttcaac cagaaaaacc         1300
Glu Arg Ser His
            420 tattgtttta aaagtgcact taagagatgg gattacaagt ggaccctga               1349
```

<210> SEQ ID NO 6
<211> LENGTH: 420
<212> TYPE: PRT
<213> ORGANISM: Homo sapiens

<400> SEQUENCE: 6

```
Met Asp Leu Ile Pro Asn Phe Ala Met Glu Thr Trp Val Leu Val Ala
1               5                   10                  15

Thr Ser Leu Val Leu Leu Tyr Ile Tyr Gly Thr His Ser His Lys Leu
            20                  25                  30

Phe Lys Lys Leu Gly Ile Pro Gly Pro Thr Pro Leu Pro Phe Leu Gly
        35                  40                  45

Thr Ile Leu Phe Tyr Leu Arg Gly Leu Trp Asn Phe Asp Arg Glu Cys
    50                  55                  60

Asn Glu Lys Tyr Gly Glu Met Trp Gly Leu Tyr Glu Gly Gln Gln Pro
65                  70                  75                  80

Met Leu Val Ile Met Asp Pro Asp Met Ile Lys Thr Val Leu Val Lys
                85                  90                  95

Glu Cys Tyr Ser Val Phe Thr Asn Gln Met Pro Leu Gly Pro Met Gly
            100                 105                 110

Phe Leu Lys Ser Ala Leu Ser Phe Ala Glu Asp Glu Glu Trp Lys Arg
        115                 120                 125

Ile Arg Thr Leu Leu Ser Pro Ala Phe Thr Ser Val Lys Phe Lys Glu
    130                 135                 140
```

```
Met Val Pro Ile Ile Ser Gln Cys Gly Asp Met Leu Val Arg Ser Leu
145                 150                 155                 160

Arg Gln Glu Ala Glu Asn Ser Lys Ser Ile Asn Leu Lys Asp Phe Phe
                165                 170                 175

Gly Ala Tyr Thr Met Asp Val Ile Thr Gly Thr Leu Phe Gly Val Asn
            180                 185                 190

Leu Asp Ser Leu Asn Asn Pro Gln Asp Pro Phe Leu Lys Asn Met Lys
        195                 200                 205

Lys Leu Leu Lys Leu Asp Phe Leu Asp Pro Phe Leu Leu Leu Ile Ser
    210                 215                 220

Leu Phe Pro Phe Leu Thr Pro Val Phe Glu Ala Leu Asn Ile Gly Leu
225                 230                 235                 240

Phe Pro Lys Asp Val Thr His Phe Leu Lys Asn Ser Ile Glu Arg Met
                245                 250                 255

Lys Glu Ser Arg Leu Lys Asp Lys Gln Lys His Arg Val Asp Phe Phe
            260                 265                 270

Gln Gln Met Ile Asp Ser Gln Asn Ser Lys Glu Thr Lys Ser His Lys
        275                 280                 285

Ala Leu Ser Asp Leu Glu Leu Val Ala Gln Ser Ile Ile Ile Ile Phe
    290                 295                 300

Ala Ala Tyr Asp Thr Thr Ser Thr Thr Leu Pro Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Val Thr Tyr Asp Ala Leu Val Gln
            340                 345                 350

Met Glu Tyr Leu Asp Met Val Val Asn Glu Thr Leu Arg Leu Phe Pro
        355                 360                 365

Val Val Ser Arg Val Thr Arg Val Cys Lys Lys Asp Ile Glu Ile Asn
    370                 375                 380

Gly Val Phe Ile Pro Lys Gly Leu Ala Val Met Val Pro Ile Tyr Ala
385                 390                 395                 400

Leu His His Asp Pro Lys Tyr Trp Thr Glu Pro Glu Lys Phe Cys Pro
                405                 410                 415

Glu Arg Ser His
            420

<210> SEQ ID NO 7
<211> LENGTH: 1633
<212> TYPE: DNA
<213> ORGANISM: Homo sapiens
<220> FEATURE:
<221> NAME/KEY: CDS
<222> LOCATION: (1)..(750)

<400> SEQUENCE: 7 atg gat ctc att cca aac ttt gcc atg gaa aca tgg gtt ctt gtg gct      48
Met Asp Leu Ile Pro Asn Phe Ala Met Glu Thr Trp Val Leu Val Ala
1               5                   10                  15 acc agc ctg gta ctc ctc tat att tat ggg acc cat tca cat aaa ctt      96
Thr Ser Leu Val Leu Leu Tyr Ile Tyr Gly Thr His Ser His Lys Leu
            20                  25                  30 ttt aag aag ctg gga att cct ggg cca acc cct ctg cct ttt ctg gga     144
Phe Lys Lys Leu Gly Ile Pro Gly Pro Thr Pro Leu Pro Phe Leu Gly
        35                  40                  45 act att ttg ttc tac ctt agg ggt ctt tgg aat ttt gac aga gaa tgt     192
Thr Ile Leu Phe Tyr Leu Arg Gly Leu Trp Asn Phe Asp Arg Glu Cys
```

-continued

| | | | | | | | | | | | | | | | | |
|---|---|---|---|---|---|---|---|---|---|---|---|---|---|---|---|---|
| | | 50 | | | | | 55 | | | | | 60 | | | | |
| aat | gaa | aaa | tac | gga | gaa | atg | tgg | ggg | ctg | tat | gag | ggg | caa | cag | ccc | 240 |
| Asn | Glu | Lys | Tyr | Gly | Glu | Met | Trp | Gly | Leu | Tyr | Glu | Gly | Gln | Gln | Pro | |
| 65 | | | | | 70 | | | | | 75 | | | | | 80 | |
| atg | ctg | gtc | atc | atg | gat | ccc | gac | atg | atc | aaa | aca | gtg | tta | gtg | aaa | 288 |
| Met | Leu | Val | Ile | Met | Asp | Pro | Asp | Met | Ile | Lys | Thr | Val | Leu | Val | Lys | |
| | | | | 85 | | | | | 90 | | | | | 95 | | |
| gaa | tgt | tac | tct | gtc | ttc | aca | aac | cag | atg | cct | tta | ggt | cca | atg | gga | 336 |
| Glu | Cys | Tyr | Ser | Val | Phe | Thr | Asn | Gln | Met | Pro | Leu | Gly | Pro | Met | Gly | |
| | | | | 100 | | | | | 105 | | | | | 110 | | |
| ttt | ctg | aaa | agt | gcc | tta | agt | ttt | gct | gaa | gat | gaa | gaa | tgg | aag | aga | 384 |
| Phe | Leu | Lys | Ser | Ala | Leu | Ser | Phe | Ala | Glu | Asp | Glu | Glu | Trp | Lys | Arg | |
| | | | | 115 | | | | | 120 | | | | | 125 | | |
| ata | cga | aca | ttg | cta | tct | cca | gct | ttc | acc | agt | gta | aaa | ttc | aag | gaa | 432 |
| Ile | Arg | Thr | Leu | Leu | Ser | Pro | Ala | Phe | Thr | Ser | Val | Lys | Phe | Lys | Glu | |
| | 130 | | | | | 135 | | | | | 140 | | | | | |
| atg | gtc | ccc | atc | att | tcc | caa | tgt | gga | gat | atg | ttg | gtg | aga | agc | ctg | 480 |
| Met | Val | Pro | Ile | Ile | Ser | Gln | Cys | Gly | Asp | Met | Leu | Val | Arg | Ser | Leu | |
| 145 | | | | | 150 | | | | | 155 | | | | | 160 | |
| agg | cag | gaa | gca | gag | aac | agc | aag | tcc | atc | aac | ttg | aaa | gat | ttc | ttt | 528 |
| Arg | Gln | Glu | Ala | Glu | Asn | Ser | Lys | Ser | Ile | Asn | Leu | Lys | Asp | Phe | Phe | |
| | | | | 165 | | | | | 170 | | | | | 175 | | |
| ggg | gcc | tac | acc | atg | gat | gta | atc | act | ggc | aca | tta | ttt | gga | gtg | aac | 576 |
| Gly | Ala | Tyr | Thr | Met | Asp | Val | Ile | Thr | Gly | Thr | Leu | Phe | Gly | Val | Asn | |
| | | | | 180 | | | | | 185 | | | | | 190 | | |
| ttg | gat | tct | ctc | aac | aat | cca | caa | gat | ccc | ttt | ctg | aaa | aat | atg | aag | 624 |
| Leu | Asp | Ser | Leu | Asn | Asn | Pro | Gln | Asp | Pro | Phe | Leu | Lys | Asn | Met | Lys | |
| | | | | 195 | | | | | 200 | | | | | 205 | | |
| aag | ctt | tta | aaa | ttg | gat | ttt | ttg | gat | ccc | ttt | tta | ctc | tta | ata | tac | 672 |
| Lys | Leu | Leu | Lys | Leu | Asp | Phe | Leu | Asp | Pro | Phe | Leu | Leu | Leu | Ile | Tyr | |
| | 210 | | | | | 215 | | | | | 220 | | | | | |
| aga | gtc | tcg | ctg | tgt | tgc | cta | ggc | cgg | agt | gca | tgg | tgc | gat | ctg | ggc | 720 |
| Arg | Val | Ser | Leu | Cys | Cys | Leu | Gly | Arg | Ser | Ala | Trp | Cys | Asp | Leu | Gly | |
| 225 | | | | | 230 | | | | | 235 | | | | | 240 | |
| tca | ctg | aaa | cct | cca | cct | cct | ggg | ttc | gag | tgattctcct | | | gcctcagcct | | | 770 |
| Ser | Leu | Lys | Pro | Pro | Pro | Pro | Gly | Phe | Glu | | | | | | | |
| | | | | 245 | | | | | 250 | | | | | | | |

| | |
|---|---|
| cctgaggagc tgggattaca gcactctttc catttcttac cccagttttt gaagccctaa | 830 |
| atatcggttt gtttccaaaa gatgttaccc atttttaaa aaattccatt gaaaggatga | 890 |
| aagaaagtcg cctcaaagat aaacaaaagc atcgagtaga tttctttcaa cagatgatcg | 950 |
| actcccagaa ttccaaagaa acaaagtccc ataaagctct gtctgatctg agcttgtgg | 1010 |
| cccagtcaat tatcatcatt tttgctgcct atgacacaac tagcaccact ctccccttca | 1070 |
| ttatgtatga actggccact caccctgatg ccagcagaa actgcaggag gagattgacg | 1130 |
| cagttttacc caataaggca cctgtcacct acgatgccct ggtacagatg gagtaccttg | 1190 |
| acatggtggt gaatgaaacg ctcagattat cccagttgt tagtagagtt acgagagtct | 1250 |
| gcaagaaaga tattgaaatc aatggagtgt cattcccaa agggttagca gtgatggttc | 1310 |
| caatctatgc tcttcaccat gacccaaagt actggacaga gctgagaag ttctgccctg | 1370 |
| aaaggttcag taagaagaac aaggacagca tagatcttta cagatacata ccttttggag | 1430 |
| ctggaccccg aaactgcatt ggcatgaggt ttgctctcac aaacataaaa cttgctgtca | 1490 |
| ttagagcact gcagaacttc tccttcaaac cttgtaaaga gactcagatc ccactgaaat | 1550 |
| tagacaatct accaattctt caaccagaaa aacctattgt tctaaaagtg cacttaagag | 1610 |
| atgggattac aagtggaccc tga | 1633 |

<210> SEQ ID NO 8
<211> LENGTH: 250
<212> TYPE: PRT
<213> ORGANISM: Homo sapiens

<400> SEQUENCE: 8

```
Met Asp Leu Ile Pro Asn Phe Ala Met Glu Thr Trp Val Leu Val Ala
 1               5                  10                  15

Thr Ser Leu Val Leu Leu Tyr Ile Tyr Gly Thr His Ser His Lys Leu
             20                  25                  30

Phe Lys Lys Leu Gly Ile Pro Gly Pro Thr Pro Leu Pro Phe Leu Gly
         35                  40                  45

Thr Ile Leu Phe Tyr Leu Arg Gly Leu Trp Asn Phe Asp Arg Glu Cys
     50                  55                  60

Asn Glu Lys Tyr Gly Glu Met Trp Gly Leu Tyr Glu Gly Gln Gln Pro
 65                  70                  75                  80

Met Leu Val Ile Met Asp Pro Asp Met Ile Lys Thr Val Leu Val Lys
                 85                  90                  95

Glu Cys Tyr Ser Val Phe Thr Asn Gln Met Pro Leu Gly Pro Met Gly
            100                 105                 110

Phe Leu Lys Ser Ala Leu Ser Phe Ala Glu Asp Glu Glu Trp Lys Arg
        115                 120                 125

Ile Arg Thr Leu Leu Ser Pro Ala Phe Thr Ser Val Lys Phe Lys Glu
    130                 135                 140

Met Val Pro Ile Ile Ser Gln Cys Gly Asp Met Leu Val Arg Ser Leu
145                 150                 155                 160

Arg Gln Glu Ala Glu Asn Ser Lys Ser Ile Asn Leu Lys Asp Phe Phe
                165                 170                 175

Gly Ala Tyr Thr Met Asp Val Ile Thr Gly Thr Leu Phe Gly Val Asn
            180                 185                 190

Leu Asp Ser Leu Asn Asn Pro Gln Asp Pro Phe Leu Lys Asn Met Lys
        195                 200                 205

Lys Leu Leu Lys Leu Asp Phe Leu Asp Pro Phe Leu Leu Leu Ile Tyr
    210                 215                 220

Arg Val Ser Leu Cys Cys Leu Gly Arg Ser Ala Trp Cys Asp Leu Gly
225                 230                 235                 240

Ser Leu Lys Pro Pro Pro Gly Phe Glu
                245                 250
```

<210> SEQ ID NO 9
<211> LENGTH: 1192
<212> TYPE: DNA
<213> ORGANISM: Homo sapiens
<220> FEATURE:
<221> NAME/KEY: CDS
<222> LOCATION: (1)..(378)

<400> SEQUENCE: 9

```
atg gat ctc att cca aac ttt gcc atg gaa aca tgg gtt ctt gtg gct      48
Met Asp Leu Ile Pro Asn Phe Ala Met Glu Thr Trp Val Leu Val Ala
 1               5                  10                  15 acc agc ctg gta ctc ctc tat att tat ggg acc cat tca cat aaa ctt      96
Thr Ser Leu Val Leu Leu Tyr Ile Tyr Gly Thr His Ser His Lys Leu
             20                  25                  30 ttt aag aag ctg gga att cct ggg cca acc cct ctg cct ttt ctg gga     144
Phe Lys Lys Leu Gly Ile Pro Gly Pro Thr Pro Leu Pro Phe Leu Gly
         35                  40                  45
```

-continued

```
act att ttg ttc tac ctt agg ggt ctt tgg aat ttt gac aga gaa tgt        192
Thr Ile Leu Phe Tyr Leu Arg Gly Leu Trp Asn Phe Asp Arg Glu Cys
     50                  55                  60 aat gaa aga ttt ctt tgg ggc cta cac cat gga tgt aat cac tgg cac        240
Asn Glu Arg Phe Leu Trp Gly Leu His His Gly Cys Asn His Trp His
 65                  70                  75                  80 att att tgg agt gaa ctt gga ttc tct caa caa tcc aca aga tcc ctt        288
Ile Ile Trp Ser Glu Leu Gly Phe Ser Gln Gln Ser Thr Arg Ser Leu
                 85                  90                  95 tct gaa aaa tat gaa gaa gct ttt aaa att gga ttt ttt gga tcc ctt        336
Ser Glu Lys Tyr Glu Glu Ala Phe Lys Ile Gly Phe Phe Gly Ser Leu
            100                 105                 110 ttt act ctt aat atc act ctt tcc att tct tac ccc agt ttt                378
Phe Thr Leu Asn Ile Thr Leu Ser Ile Ser Tyr Pro Ser Phe
        115                 120                 125 tgaagcccta aatatcggtt tgtttccaaa agatgttacc cattttttaa aaaattccat      438
tgaaaggatg aaagaaagtc gcctcaaaga taaacaaaag catcgagtag atttctttca      498
acagatgatc gactcccaga attccaaaga aacaaagtcc cataaagctc tgtctgatct      558
ggagcttgtg gcccagtcaa ttatcatcat ttttgctgcc tatgacacaa ctagcaccac      618
tctcccttc attatgtatg aactggccac tcacctgat gtccagcaga aactgcagga       678
ggagattgac gcagttttac ccaataaggc acctgtcacc tacgatgccc tggtacagat      738
ggagtacctt gacatggtgg tgaatgaaac gctcagatta ttcccagttg ttagtagagt      798
tacgagagtc tgcaagaaag atattgaaat caatggagtg ttcattccca aagggttagc      858
agtgatggtt ccaatctatg ctcttcacca tgacccaaag tactgagcag agcctgagaa      918
gttctgccct gaaaggttca gtaagaagaa caaggacagc atagatcttt acagatacat      978
acctttgga gctggacccc gaaactgcat tggcatgagg tttgctctca caaacataaa     1038
acttgctgtc attagagcac tgcagaactt ctccttcaaa ccttgtaaag agactcagat     1098
cccactgaaa ttagacaatc taccaattct tcaaccagaa aaacctattg ttctaaaagt     1158
gcacttaaga gatgggatta caagtggacc ctga                                1192
```

<210> SEQ ID NO 10
<211> LENGTH: 126
<212> TYPE: PRT
<213> ORGANISM: Homo sapiens

<400> SEQUENCE: 10

```
Met Asp Leu Ile Pro Asn Phe Ala Met Glu Thr Trp Val Leu Val Ala
 1               5                  10                  15

Thr Ser Leu Val Leu Leu Tyr Ile Tyr Gly Thr His Ser His Lys Leu
                20                  25                  30

Phe Lys Lys Leu Gly Ile Pro Gly Pro Thr Pro Leu Pro Phe Leu Gly
            35                  40                  45

Thr Ile Leu Phe Tyr Leu Arg Gly Leu Trp Asn Phe Asp Arg Glu Cys
        50                  55                  60

Asn Glu Arg Phe Leu Trp Gly Leu His His Gly Cys Asn His Trp His
 65                  70                  75                  80

Ile Ile Trp Ser Glu Leu Gly Phe Ser Gln Gln Ser Thr Arg Ser Leu
                 85                  90                  95

Ser Glu Lys Tyr Glu Glu Ala Phe Lys Ile Gly Phe Phe Gly Ser Leu
            100                 105                 110

Phe Thr Leu Asn Ile Thr Leu Ser Ile Ser Tyr Pro Ser Phe
```

<210> SEQ ID NO 11
<211> LENGTH: 1973
<212> TYPE: DNA
<213> ORGANISM: Homo sapiens
<220> FEATURE:
<221> NAME/KEY: CDS
<222> LOCATION: (1)..(222)
<223> OTHER INFORMATION: n=a, c, t or g

<400> SEQUENCE: 11

| | | | | | | | | | | | | | | | | |
|---|---|---|---|---|---|---|---|---|---|---|---|---|---|---|---|---|
| atg | gat | ctc | att | cca | aac | ttt | gcc | atg | gaa | aca | tgg | gtt | ctt | gtg | gct | 48 |
| Met | Asp | Leu | Ile | Pro | Asn | Phe | Ala | Met | Glu | Thr | Trp | Val | Leu | Val | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | agc | ctg | gta | ctc | ctc | tat | att | tat | ggg | acc | cat | tca | cat | aaa | ctt | 96 |
| Thr | Ser | Leu | Val | Leu | Leu | Tyr | Ile | Tyr | Gly | Thr | His | Ser | His | Lys | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| ttt | aag | aag | ctg | gga | att | cct | ggg | cca | acc | cct | ctg | cct | ttt | ctg | gga | 144 |
| Phe | Lys | Lys | Leu | Gly | Ile | Pro | Gly | Pro | Thr | Pro | Leu | Pro | Phe | Leu | Gly | |
| | 35 | | | | | 40 | | | | | 45 | | | | | |

| | | | | | | | | | | | | | | | | |
|---|---|---|---|---|---|---|---|---|---|---|---|---|---|---|---|---|
| act | att | ttg | ttc | tac | ctt | agg | ggt | ctt | tgg | aat | ttt | gac | aga | gaa | tgt | 192 |
| Thr | Ile | Leu | Phe | Tyr | Leu | Arg | Gly | Leu | Trp | Asn | Phe | Asp | Arg | Glu | Cys | |
| | 50 | | | | | 55 | | | | | 60 | | | | | |

| | | | | | | | | |
|---|---|---|---|---|---|---|---|---|
| aat | gaa | aaa | tac | gga | gaa | atg | tgg | ggc | cct | taggtccaat | gggatttctg | 242 |
| Asn | Glu | Lys | Tyr | Gly | Glu | Met | Trp | Gly | Pro | | | |
| 65 | | | | | 70 | | | | | | | |

| | |
|---|---|
| aaaagtgcct taagttttgc tgaagatgaa gaatggaaga gaatacgaac attgctatct | 302 |
| ccagctttca ccagtgtaaa attcaaggaa gtaagaaaat aaggtgattt ataattagaa | 362 |
| acttaaagga tgaatctgga gacaggtagt aagtatcatc atagttcctt tctaatgggt | 422 |
| agtccactga gtttgagctt tctaaaaagg gtcttttcag ctgggcacag tggctcatgc | 482 |
| ctgtaatccc agcactttgg gaggccgagg tgggtggatc acctgaggtt aggagattga | 542 |
| gaccagcctg gccaacatgg tgaaacccca actctactaa aaatacaaaa attagctggg | 602 |
| catggtggcg gatgcctata atcctagctg ctcagaaggc taaggcagaa gaattgtttg | 662 |
| aatctagagg cggaggttgc aatgagccaa gattgcgccg ttgcactnca gcctgggcaa | 722 |
| caagagcgaa actctgtctc aaaaaaaang gcaggggggc ggtctttcct atttatgtcc | 782 |
| tagaggacat ggtgagtcat tacaaaatat catttactgg tncatgctgg gcaaagccat | 842 |
| gtccttctga gactcgagtc tgcgtagtta actatgggtg gngtgggttt tagangggccc | 902 |
| catcatttcc caatgtggag atatgttggt gagaagcctg aggcaggaag cagagaacag | 962 |
| caagtccatc aacttgaaag atttctttgg ggcctacacc atggatgtaa tcactggcac | 1022 |
| attatttgga gtgaacttgg attctctcaa caatccacaa gatcccttc tgaaaaatat | 1082 |
| gaagaagctt ttaaaattgg attttttgga tcccttttta ctcttaatat cactcttttcc | 1142 |
| atttcttacc ccagttttg aagccctaaa tatcggtttg tttccaaaag atgttaccca | 1202 |
| ttttttaaaa aattccattg aaaggatgaa agaaagtcgc ctcaaagata aacaaaagca | 1262 |
| tcgagtagat ttctttcaac agatgatcga ctcccagaat tccaagaaa caaagtccca | 1322 |
| taaagctctg tctgatctgg agcttgtggc ccagtcaatt atcatcattt tgctgcctta | 1382 |
| tgacacaact agcaccactc tccccttcat tatgtatgaa ctggccactc accctgatgt | 1442 |
| ccagcagaaa ctgcaggagg agattgacgc agttttaccc aataaggcac ctgtcaccta | 1502 |
| cgatgccctg gtacagatgg agtaccttga catggtggtg aatgaaacgc tcagattatt | 1562 |
| cccagttgtt agtagagtta cgagagtctg caagaaagat attgaaatca atggagtgtt | 1622 |

```
cattcccaaa gggttagcag tgatggttcc aatctatgct cttcaccatg acccaaagta      1682
ctggacagag cctgagaagt tctgccctga aggttcagt aagaagaaca aggacagcat       1742
agatctttac agatacatac cttttggagc tggaccccga aactgcattg gcatgaggtt      1802
tgctctcaca aacataaaac ttgctgtcat tagagcactg cagaacttct ccttcaaacc      1862
ttgtaaagag actcagatcc cactgaaatt agacaatcta ccaattcttc aaccagaaaa     1922
cctattgttc taaaagtgca cttaagagat gggattacaa gtggaccctg a              1973
```

<210> SEQ ID NO 12
<211> LENGTH: 74
<212> TYPE: PRT
<213> ORGANISM: Homo sapiens

<400> SEQUENCE: 12

```
Met Asp Leu Ile Pro Asn Phe Ala Met Glu Thr Trp Val Leu Val Ala
  1               5                  10                  15
Thr Ser Leu Val Leu Tyr Ile Tyr Gly Thr His Ser His Lys Leu
             20                  25                  30
Phe Lys Lys Leu Gly Ile Pro Gly Pro Thr Pro Leu Pro Phe Leu Gly
         35                  40                  45
Thr Ile Leu Phe Tyr Leu Arg Gly Leu Trp Asn Phe Asp Arg Glu Cys
     50                  55                  60
Asn Glu Lys Tyr Gly Glu Met Trp Gly Pro
 65                  70
```

<210> SEQ ID NO 13
<211> LENGTH: 20
<212> TYPE: DNA
<213> ORGANISM: Homo sapiens

<400> SEQUENCE: 13

```
aacaggcgtg gaaacacaat                                                    20
```

<210> SEQ ID NO 14
<211> LENGTH: 18
<212> TYPE: DNA
<213> ORGANISM: Homo sapiens

<400> SEQUENCE: 14

```
ctttcctgcc ctgcacag                                                      18
```

<210> SEQ ID NO 15
<211> LENGTH: 20
<212> TYPE: DNA
<213> ORGANISM: Homo sapiens

<400> SEQUENCE: 15

```
atatggaacc cattcacatg                                                    20
```

<210> SEQ ID NO 16
<211> LENGTH: 23
<212> TYPE: DNA
<213> ORGANISM: Homo sapiens

<400> SEQUENCE: 16

```
caggctgttg accatcataa aag                                                23
```

<210> SEQ ID NO 17
<211> LENGTH: 21

<212> TYPE: DNA
<213> ORGANISM: Homo sapiens

<400> SEQUENCE: 17
ctatgacaca actagcacca c                                          21

<210> SEQ ID NO 18
<211> LENGTH: 21
<212> TYPE: DNA
<213> ORGANISM: Homo sapiens

<400> SEQUENCE: 18
catagattgg aaccatcact g                                          21

<210> SEQ ID NO 19
<211> LENGTH: 24
<212> TYPE: DNA
<213> ORGANISM: Homo sapiens

<400> SEQUENCE: 19
ggctctccag aacatcatcc ctgc                                       24

<210> SEQ ID NO 20
<211> LENGTH: 24
<212> TYPE: DNA
<213> ORGANISM: Homo sapiens

<400> SEQUENCE: 20
gggtgtcgct gttgaagtca gagg                                       24

<210> SEQ ID NO 21
<211> LENGTH: 25
<212> TYPE: DNA
<213> ORGANISM: Homo sapiens

<400> SEQUENCE: 21
gaggagtacc aggctggtag ccaca                                      25

<210> SEQ ID NO 22
<211> LENGTH: 26
<212> TYPE: DNA
<213> ORGANISM: Homo sapiens

<400> SEQUENCE: 22
gcacaggctg ttgaccatca taaaag                                     26

<210> SEQ ID NO 23
<211> LENGTH: 26
<212> TYPE: DNA
<213> ORGANISM: Homo sapiens

<400> SEQUENCE: 23
cagggagttg accttcatac gttccc                                     26

<210> SEQ ID NO 24
<211> LENGTH: 26
<212> TYPE: DNA
<213> ORGANISM: Homo sapiens

<400> SEQUENCE: 24
gcataggctg ttgacagtca taaata                                     26

<210> SEQ ID NO 25

-continued

```
<211> LENGTH: 20
<212> TYPE: DNA
<213> ORGANISM: Homo sapiens

<400> SEQUENCE: 25
aacagcacac agctgaaagt                                                 20

<210> SEQ ID NO 26
<211> LENGTH: 20
<212> TYPE: DNA
<213> ORGANISM: Homo sapiens

<400> SEQUENCE: 26
ctgatggtag gacaaagtag                                                 20

<210> SEQ ID NO 27
<211> LENGTH: 26
<212> TYPE: DNA
<213> ORGANISM: Homo sapiens

<400> SEQUENCE: 27
cctggtgctc ctctatctat atggag                                          26

<210> SEQ ID NO 28
<211> LENGTH: 22
<212> TYPE: DNA
<213> ORGANISM: Homo sapiens

<400> SEQUENCE: 28
gggagttgac cttcatacgt tc                                              22

<210> SEQ ID NO 29
<211> LENGTH: 20
<212> TYPE: DNA
<213> ORGANISM: Homo sapiens

<400> SEQUENCE: 29
caaactttgc catggaaatg                                                 20

<210> SEQ ID NO 30
<211> LENGTH: 30
<212> TYPE: DNA
<213> ORGANISM: Homo sapiens

<400> SEQUENCE: 30
ttgaggcgac tttctttcat cctttcaatg                                      30

<210> SEQ ID NO 31
<211> LENGTH: 19
<212> TYPE: DNA
<213> ORGANISM: Homo sapiens

<400> SEQUENCE: 31
aaatcttggc attccaggt                                                  19

<210> SEQ ID NO 32
<211> LENGTH: 23
<212> TYPE: DNA
<213> ORGANISM: Homo sapiens

<400> SEQUENCE: 32
taggctgttg acagtcataa ata                                             23
```

<210> SEQ ID NO 33
<211> LENGTH: 21
<212> TYPE: DNA
<213> ORGANISM: Homo sapiens

<400> SEQUENCE: 33
gctctccaag gttttagatg c                                        21

<210> SEQ ID NO 34
<211> LENGTH: 19
<212> TYPE: DNA
<213> ORGANISM: Homo sapiens

<400> SEQUENCE: 34
gggagtgcca cacttgttc                                           19

<210> SEQ ID NO 35
<211> LENGTH: 475
<212> TYPE: DNA
<213> ORGANISM: Homo sapiens

<400> SEQUENCE: 35
gaacctgaag tctataggta gagaaaattg taattgttgt aggtaaattt cacattttc    60 actatgattt attttttctt tttctattta attttcctat agcactcttt ccatttctta  120
ccccagtttt tgaagcccta aatatcggtt tgtttccaaa agatgttacc cattttttaa  180
aaaattccat tgaaaggatg aaagaaagtc gcctcaaaga taaacaaaag catcgagtag  240
atttctttca acagatgatc gactcccaga attccaaaga aacaaagtcc cataaagctc  300
tgtctgatct ggagcttgtg gcccagtcaa ttatcatcat ttttgctgcc tatgacacaa  360
ctagcaccac tctccccttc attatgtatg aactggccac tcacctgat gtccagcaga   420 aactgcagga ggagattgac gcattttacc caataaggca cctgtcacct acgat       475

<210> SEQ ID NO 36
<211> LENGTH: 531
<212> TYPE: DNA
<213> ORGANISM: Homo sapiens

<400> SEQUENCE: 36
tttaagctca tcttcatttc tgagtttat tcacaaaaca atttgaagtg tctagtgttc    60
tgggatacag ctttcttgaa caaagtggaa gtccttaggg aaagtcaggg tccacttgta  120
atcccatctc ttaagtgcac ttttagaaca ataggttttt ctggttgaag aattggtaga  180
ttgtctaatt tcagtgggat ctgagtctct ttacaaggtt tgaaggagaa gttctgcagt  240
gctctaatga cagcaagttt tatgtttgtg agagcaaacc tcatgccaat gcagtttcgg  300
ggtccagctc caaaggtat gtatctgtaa agatctatgc tgtccttgtt cttcttactg    360 aaccttcag gcagaacttt tcaggctct gtccagtact ttgggtcatg gtgaagagca    420
tagattggaa ccatcactgc taacccttg ggaatgaaca ctccattgat ttcaatatct   480
ttcttgcaga ctctcgtaac tctactaaca actggggaat atctgagcgt t            531

<210> SEQ ID NO 37
<211> LENGTH: 169
<212> TYPE: DNA
<213> ORGANISM: Homo sapiens
<220> FEATURE:
<221> NAME/KEY: misc_feature
<222> LOCATION: (1)...(169)
<223> OTHER INFORMATION: n=a, c, t or g

<400> SEQUENCE: 37

```
tctaagttca gtgggatctg agtctcttta caaggtttga aggagangtt ctgcagtgcn      60
ctantgacag caagttttat gtttgtgaga gcaaacctca ngccaatgca gtttcggggt     120
ccagctccna naggnntgta tctgtaaagn nctatgctgt ccttgttct                 169
```

<210> SEQ ID NO 38
<211> LENGTH: 299
<212> TYPE: DNA
<213> ORGANISM: Homo sapiens
<220> FEATURE:
<221> NAME/KEY: misc_feature
<222> LOCATION: (1)...(299)
<223> OTHER INFORMATION: n=a, c, t or g

<400> SEQUENCE: 38

```
attgcggcac aggcgnnacc aggtgtcagg aactgggcca ggcagtgaga aatccatata      60
ctaaaaaaag nctgttgtna agaatgtntg acatacacat aactatatnc tatagacacc    120
aggctataga acagtattag tgcatccccc tgtgttcatc acctgtctca gtagtcaatg    180
ctgcatgtca gcttgccctg tccacacacc accacantcc tctctgtgac tacaatgtta    240
tcttgnagat aataacctgt aaatatttca gagttttctc taaaatataa gtagtcttt     299
```

<210> SEQ ID NO 39
<211> LENGTH: 106
<212> TYPE: DNA
<213> ORGANISM: Homo sapiens

<400> SEQUENCE: 39

```
actgctgtgc agggcaggaa agctccatgc acatagccca gcaaagagca acacagagct      60
gaaaggaaga ctcagaggag agagataagt aaggaaagta gtgatg                   106
```

<210> SEQ ID NO 40
<211> LENGTH: 106
<212> TYPE: DNA
<213> ORGANISM: Homo sapiens

<400> SEQUENCE: 40

```
actgctgtgc agggcaggaa agctccacac acacagccca gcaaacagca gcacgctgct      60
gaaaaaaaga ctcagaggag agagataagg aaggaaagta gtgatg                   106
```

<210> SEQ ID NO 41
<211> LENGTH: 105
<212> TYPE: DNA
<213> ORGANISM: Homo sapiens

<400> SEQUENCE: 41

```
ctgctgtgca gggcagggaa gctccaggca aacagcccag caaacagcag cactcagcta      60
aaaggaagac tcacagaaca cagttgaaga aggaaagtgg cgatg                    105
```

<210> SEQ ID NO 42
<211> LENGTH: 106
<212> TYPE: DNA
<213> ORGANISM: Homo sapiens

<400> SEQUENCE: 42

```
acctctgggc agagaaacaa agctctatat gcacagccca gcaaagagca gcacacagct      60
gaaagaaaaa ctcagaagac agagctgaaa agaaaaactg gtgatg                   106
```

```
<210> SEQ ID NO 43
<211> LENGTH: 673
<212> TYPE: DNA
<213> ORGANISM: Homo sapiens

<400> SEQUENCE: 43
ggaagttgtg tccaaaggcc agagaagctg aggatcaggg agagcaaaga ctaaaaagca      60
gatagacatg acaaaaggat ttctctcaag gaaacatcct gctctccaag gttttagatg     120
catgatttta ttctaaacat tggtgactca ggcaacaccc attacacttc tgaacttaaa     180
gagagcatat tctcaggagg ggtgcttagg actggactcc tgattcactt ctgacttcac     240
aagtgacttt ctgtcattaa aatttctctt tttgcttcca gcatcgagta gatttctttc     300
aacagatgat cgactcccag aattccaaag aaacaaagtc ccataaaggt aaccaagaac     360
tgcatctggg ggctactgat ggggacactc agagagaagg ccctgttctg aaaatgtgca     420
gaaagttttc caggaaaatg agaatttctt ccacattgca gaaaggcaca catttggatg     480
ttataaatga tagctggagg cactttctag aagcacacag gcatagccac attccaggct     540
tgaagggcaa ccctgaacaa gtgtggcact cccggaggtc ggtcagtgat ctgtggatca     600
cccacatcag ataaaatgcc agttctcagc ctcctccaga tccacttact cagaacttgg     660
aaacgtacat cta                                                        673

<210> SEQ ID NO 44
<211> LENGTH: 48
<212> TYPE: DNA
<213> ORGANISM: Homo sapiens

<400> SEQUENCE: 44
gtagatttct ttcaacagat gatcgactcc cagaattcca aagaaaca                   48

<210> SEQ ID NO 45
<211> LENGTH: 48
<212> TYPE: DNA
<213> ORGANISM: Homo sapiens
<220> FEATURE:
<221> NAME/KEY: misc_feature
<222> LOCATION: (1)...(48)
<223> OTHER INFORMATION: n=a, c, t or g

<400> SEQUENCE: 45
gtagatttct ttcaacagat natcgactcc cagaattcca aagaaaca                   48
```